US011109793B2

(12) United States Patent
Kaib et al.

(10) Patent No.: US 11,109,793 B2
(45) Date of Patent: Sep. 7, 2021

(54) MEDICAL DEVICE FOR SENSING CARDIAC FUNCTION

(71) Applicant: ZOLL Medical Corporation, Chelmsford, MA (US)

(72) Inventors: Thomas E Kaib, Irwin, PA (US); Shane S Volpe, Saltsburg, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 27 days.

(21) Appl. No.: 16/445,400

(22) Filed: Jun. 19, 2019

(65) Prior Publication Data

US 2019/0298214 A1    Oct. 3, 2019

Related U.S. Application Data

(63) Continuation of application No. 16/038,800, filed on Jul. 18, 2018, now Pat. No. 10,368,768, which is a continuation of application No. 15/081,170, filed on Mar. 25, 2016, now Pat. No. 10,052,043.

(Continued)

(51) Int. Cl.
*A61B 5/0452* (2006.01)
*A61B 5/046* (2006.01)
(Continued)

(52) U.S. Cl.
CPC .................. *A61B 5/35* (2021.01); *A61B 5/25* (2021.01); *A61B 5/361* (2021.01); *A61B 5/363* (2021.01);
(Continued)

(58) Field of Classification Search
CPC ....... A61B 5/0402; A61B 5/0472; A61B 5/00; A61B 5/046; A61B 5/0408; A61B 5/0452;
(Continued)

(56) References Cited

U.S. PATENT DOCUMENTS 5,944,669 A    8/1999 Kalb
2002/0087091 A1    7/2002 Koyrakh et al.
(Continued)

OTHER PUBLICATIONS

International Search Report and Written Opinion from corresponding International Application No. PCT/US2016/024165 dated Jun. 23, 2016.

*Primary Examiner* — Jon Eric C Morales
(74) *Attorney, Agent, or Firm* — ZOLL Medical Corporation

(57) ABSTRACT

A medical device includes at least one electrode to sense an electrocardiogram (ECG) signal of a patient, and a controller coupled to the at least one electrode. The controller is configured to generate a first ECG template based on a first ECG signal of the patient received during a first baselining operation. The controller is configured to determine that the patient has been administered a therapeutic shock, and responsive to the determination that the patient has been administered the therapeutic shock, the controller is configured to initiate a second baselining operation and generate a second ECG template based on a second ECG signal of the patient received during the second baselining operation. The controller is configured to determine whether the patient is experiencing a cardiac event based on a comparison of the second ECG template to a real time ECG signal received during real time monitoring of the patient.

20 Claims, 9 Drawing Sheets

Related U.S. Application Data

(60) Provisional application No. 62/139,318, filed on Mar. 27, 2015.

(51) Int. Cl.
*A61B 5/0464* (2006.01)
*A61B 5/35* (2021.01)
*A61B 5/00* (2006.01)
*A61B 5/25* (2021.01)
*A61B 5/361* (2021.01)
*A61B 5/363* (2021.01)
*A61B 5/366* (2021.01)

(52) U.S. Cl.
CPC ............ *A61B 5/366* (2021.01); *A61B 5/6805* (2013.01); *A61B 5/7221* (2013.01); *A61B 5/7282* (2013.01); *A61B 5/746* (2013.01)

(58) Field of Classification Search
CPC . A61B 4/0464; A61B 5/04525; A61B 5/7221; A61B 5/4836; A61B 5/6805; A61B 5/7282; A61B 7/46
See application file for complete search history.

(56) References Cited

U.S. PATENT DOCUMENTS

| | | |
|---|---|---|
| 2008/0234770 A1 | 9/2008 | Kim et al. |
| 2009/0270747 A1 | 10/2009 | van Dam et al. |
| 2009/0275850 A1 | 11/2009 | Mehendale et al. |
| 2010/0331904 A1 | 12/2010 | Warren et al. |
| 2011/0034817 A1 | 2/2011 | Marcovecchio |
| 2012/0289847 A1 | 11/2012 | Zhang et al. |

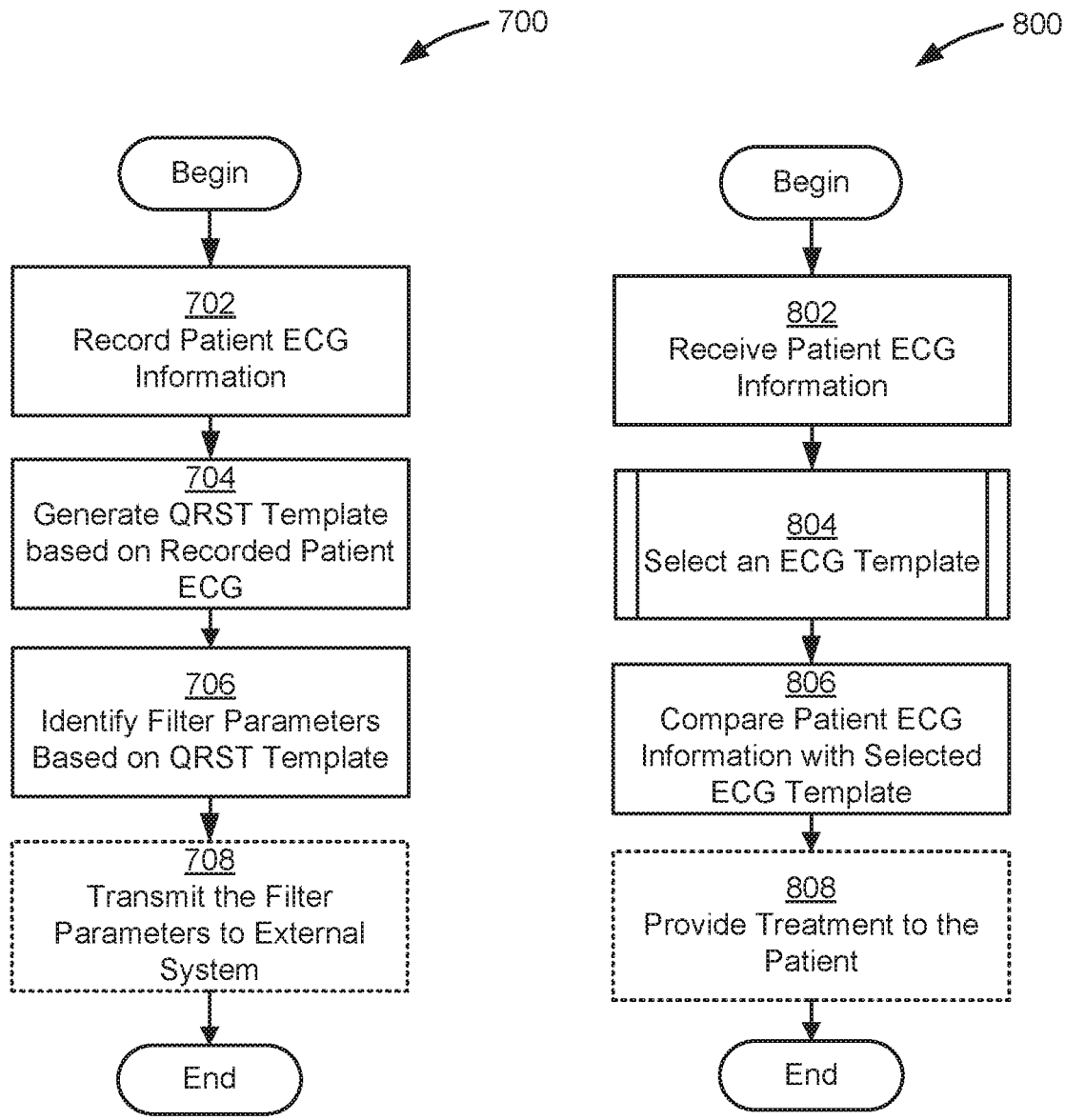

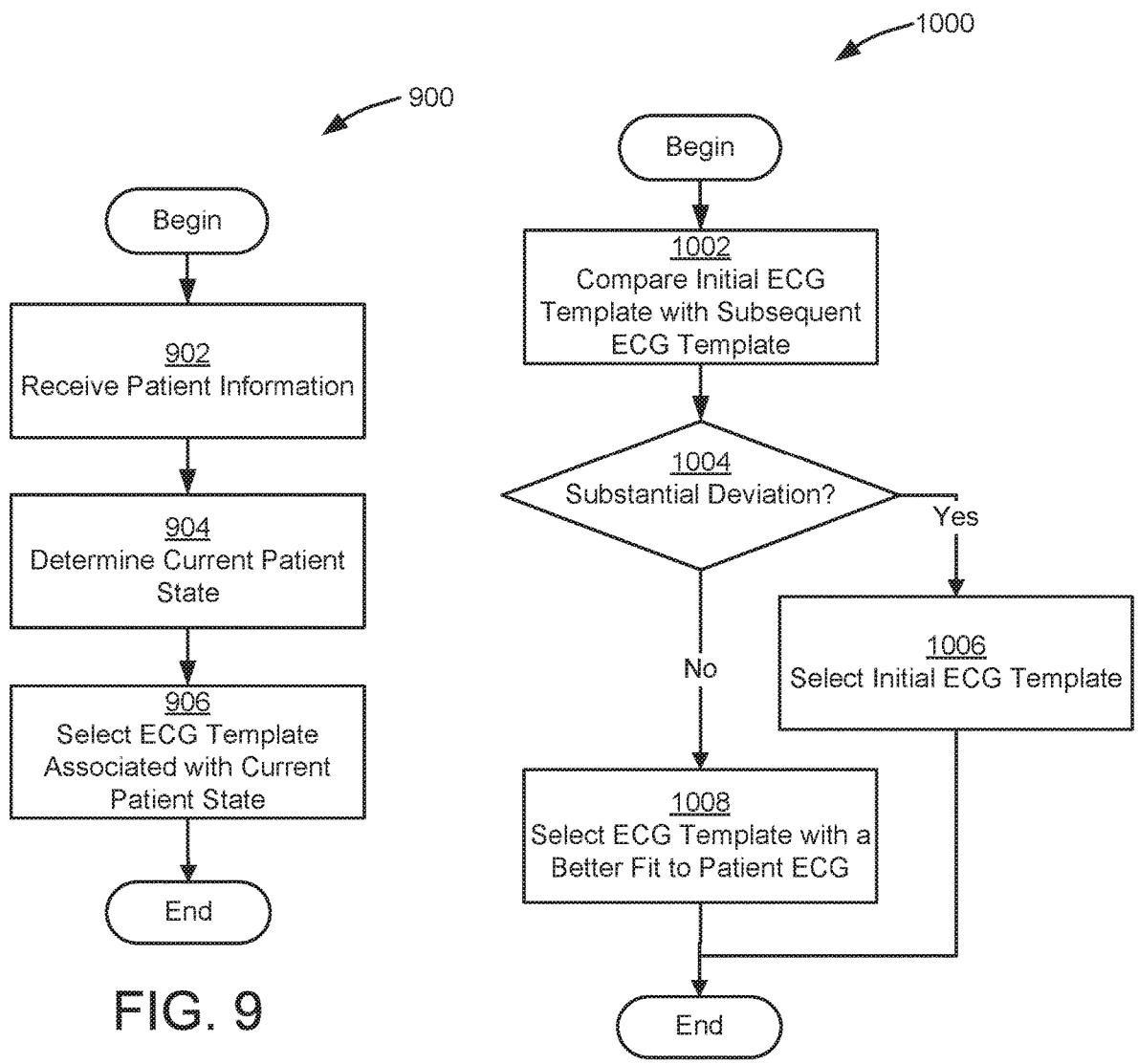

MEDICAL DEVICE FOR SENSING CARDIAC FUNCTION

RELATED APPLICATIONS

This application claims the benefit under 35 U.S.C. § 120 as a continuation of U.S. application Ser. No. 16/038,800, titled "MEDICAL DEVICE FOR SENSING CARDIAC FUNCTION," filed Jul. 18, 2018, which is a continuation of U.S. application Ser. No. 15/081,170, titled "MEDICAL DEVICE FOR SENSING CARDIAC FUNCTION," filed Mar. 25, 2016, now U.S. Pat. No. 10,052,043, which claims priority under 35 U.S.C. § 119(e) to U.S. Provisional Application Ser. No. 62/139,318, titled "MEDICAL DEVICE FOR SENSING CARDIAC FUNCTION," filed Mar. 27, 2015, each of which is hereby incorporated herein by reference in its entirety.

BACKGROUND

Technical Field

This disclosure relates to medical devices, and more particularly to medical devices that monitor patient cardiac function.

Discussion

Many cardiac patients have conditions which can result in excessively fast or erratic heartbeats. If not treated promptly, ventricular fibrillation or certain ventricular tachycardias can result in a fatal outcome. If such arrhythmias are promptly detected and treated, such as by electric shock defibrillation, the result of such an attack can often be minimized. Treatment is normally needed within a few minutes of the onset of the condition to be effective. Therefore, it can be critical to accurately detect such a condition as soon as possible after its occurrence.

Ventricular tachycardia and ventricular fibrillation are two heart rhythms that are treatable by an electrical shock properly applied to the body of the patient. Both of these conditions sometimes occur along with a detectable high heart rate in the patient. Utilization of a threshold heart rate will detect these two conditions in many cases and treatment can begin. Unfortunately, other conditions such as, for example, supraventricular tachycardia also have a high heart rate and these are not treatable by electric shock therapy. Therefore, utilizing a detection methodology which relies only on heart rate to institute treatment may cause treatment to be rendered under conditions where shock therapy may be inappropriate.

SUMMARY

Some aspects and examples herein accurately identify cardiac events experienced by a patient by comparing the electrocardiogram (ECG) signal of the patient with one or more ECG templates associated with the patient. For example, medical devices in accord with some examples generate an electrocardiogram (ECG) template for the patient based on recorded patient ECG information while the patient is not experiencing a cardiac condition (e.g., ventricular fibrillation, ventricular tachycardia, or supraventricular tachycardia). The generated ECG template may be compared with the ECG signal of the patient by constructing a matched filter based on the ECG template and filtering the patient ECG signal. The output of the matched filter may be a correlation between the patient ECG signal and the ECG template that may be analyzed to determine whether the patient is experiencing a cardiac condition and/or identify a specific type of cardiac condition.

In some examples, the medical device updates the ECG templates as appropriate for the patient. Updating the ECG template may be advantageous because the sinus rhythm of a patient may change as the activity levels of a patient change. A patient who has lost weight by exercising may experience a change in normal sinus rhythm. The medical device may update the ECG template, for example, periodically or aperiodically. It is appreciated that the generation of a new ECG template may be triggered by detection of a particular event. For example, a user interface of the medical device may permit the patient (or a caretaker of the patient) to initiate various ECG template generation processes. The medical device may also detect that a different patient is using the medical device and, in response, initiate an ECG template generation process.

According to at least one aspect, a medical device is provided. The medical device includes at least one electrode to sense an electrocardiogram (ECG) signal of a patient and a controller coupled to the at least one electrode. The controller may be configured to generate a first ECG template based on a first ECG signal of the patient, generate a second ECG template based on a second ECG signal of the patient, and determine whether the patient is experiencing a cardiac event based on the ECG signal of the patient and an identified one of the first ECG template and the second ECG template.

In one example, the ECG signals for use in determining whether the patient is experiencing a cardiac event can be acquired from real time monitoring of the patient. In one example, the controller is configured to perform a convolution operation on the ECG signal and at least one of the first and second ECG templates to determine whether one or more characteristics of the ECG signal indicate either the presence or absence of the cardiac event. In one example, at least one of the first and the second ECG signals are received during operation of a baselining mode of the medical device. In on example, the ECG signal is received during operation of a monitoring mode of the medical device.

In one example, the controller is configured to compare the second ECG template with the first ECG template to generate a comparison, determine a quality score corresponding to the second ECG template based on the comparison, and, based on the quality score, identify the second ECG template as the at least one of the first ECG template and the second ECG template for a subsequent determination of whether the patient is experiencing a cardiac event. In one example, the controller is configured to determine whether the patient is experiencing the cardiac event in part based on one or more morphological differences between the ECG signal and one or more of the first and second ECG templates.

In one example, the controller is configured to generate the second ECG template during a second time period that is different from a first time period in which the first ECG template is generated. In this example, the second time period may occur subsequently to the first time period and the second time period may span a different duration than the first time period.

In one example, the controller is configured to generate the second ECG template on a predetermined schedule. In one example, the controller is configured to generate the second ECG template during a baselining operation initiated by one of a remote server, a human operator, and the patient.

In one example, the controller is configured to provide a notification prior to generating at least one of the first ECG template and the second ECG template by a baselining operation.

In one example, the controller is configured to generate at least one ECG template of the first and second ECG templates by determining numerical coefficients of one or more matched filters based on analysis of an identified ECG signal corresponding to the at least one ECG template. In this example, the controller may be configured to determine whether the patient is experiencing a cardiac event based in part by filtering the ECG signal with at least one of the one or more matched filters.

In one example, the controller is configured to read a parameter that specifies a delay between generation of the first ECG template and generation of the second ECG template. In one example, the controller is configured to compare the first ECG template to the second ECG template and to discard the second ECG template responsive the second ECG template deviating from the first ECG template by a threshold measurement. In one example, the controller is configured to associate the first ECG template with a first patient, associate the second ECG template with a second patient, and to identify the at least one of the first ECG template and the second ECG template based on an automatic determination of an identity of a patient as either the first or second patient from the patient's ECG signal.

In one example, the medical device includes a motion detector to detect and record historical information relating to a patient's movement and the controller is configured to identify the at least one of the first ECG template and the second ECG template based on the historical information relating to the patient's movement. In this example, the controller may be configured to calculate an activity score based on the historical information relating to the patient's movement, and to identify the at least one of the first ECG template and the second ECG template based on the activity score.

In one example, the medical device includes at least one antenna coupled to the controller and the controller is configured to transmit, via the at least one antenna, one or more of the first ECG template and the second ECG template to an external system. In one example, the medical device includes at least one antenna coupled to the controller and wherein the controller is configured to receive, from an external system via the at least one antenna, one or more of the first ECG template and the second ECG template.

In one example, the medical device includes at least two electrode pairs and the controller is configured to determine whether the patient is experiencing the cardiac event by comparing each pair of signals from the at least two electrode pairs with either the first ECG template or the second ECG template using one or more matched filters. In this example, the controller is configured to perform a signal operation based on the one or more matched filters on each pair of signals from the at least two electrode pairs and either the first ECG template or the second ECG template. The signal operation may include, for example, a convolution operation on a pair of signals and either the first ECG template or the second ECG template.

In one example, the controller is configured to determine whether the cardiac event is a treatable arrhythmia or an untreatable arrhythmia by performing a morphology analysis of the ECG signal with respect to the at least one of the first ECG template and the second ECG template. The treatable arrhythmia may include, for example, either ventricular tachycardia or ventricular fibrillation and the untreatable arrhythmia may include, for example, supraventricular tachycardia. In this example, the morphology analysis may include detecting a QRS complex in the ECG signal, and where the QRS complex is detected, determining that the cardiac event is an untreatable arrhythmia. It is appreciated that detecting the QRS complex may include performing a convolution operation on the ECG signal and at least one of the first and second ECG signals to determine whether one or more characteristics in the ECG signal indicate either presence or absence of the QRS complex.

In one example, the medical device comprises one of a wearable defibrillator, an in-hospital defibrillator, a mobile cardiac telemetry monitor, and an automated external defibrillator. In one example, the cardiac event includes at least one of premature ventricular contraction (PVC), ventricular fibrillation (VF), ventricular tachycardia (VT), and supraventricular tachycardia (SVT).

According to at least one aspect, a medical device is provided. The medical device includes at least one electrode to sense an electrocardiogram (ECG) signal of a patient and a detection component. The detection component may be configured to generate a first ECG template based on a first ECG signal of the patient, generate a second ECG template based on a second ECG signal of the patient, and determine whether the patient is experiencing a cardiac event based on the ECG signal of the patient and an identified one of the first ECG template and the second ECG template.

In one example, the ECG signals for use in determining whether the patient is experiencing a cardiac event can be acquired from real time monitoring of the patient. In one example, determining whether the patient is experiencing the cardiac event includes performing a convolution operation on a signal representation of the ECG signal and a corresponding signal representation of at least one of the first and second ECG templates to determine whether one or more characteristics of the ECG signal indicate either the presence or absence of the cardiac event. In one example, at least one of the first and the second ECG signals are received during operation of a baselining mode of the medical device. In one example, at least the ECG signal is received during operation of a monitoring mode of the medical device.

In one example, the detection component is further configured to compare the second ECG template with the first ECG template to generate a comparison, determine a quality score corresponding to the second ECG template based on the comparison, and based on the quality score, identify the second ECG template as the at least one of the first ECG template and the second ECG template for a subsequent determination of whether the patient is experiencing a cardiac event.

In one example, determining whether the patient is experiencing the cardiac event includes to determine whether the patient is experiencing the cardiac event in part based on one or more morphological differences between the ECG signal and one or more of the first and second ECG templates.

In one example, the second ECG template is generated during a second time period that is different from a first time period in which the first ECG template is generated. In this example, the second time period may occur subsequently to the first time period. In addition, the second time period may span a different duration than the first time period.

In one example, generating the second ECG template includes generating the second ECG template on a predetermined schedule. In one example, generating the second ECG template includes generating the second ECG template during a baselining operation initiated by a remote server. In one example, generating the second ECG template includes generating the second ECG template during a baselining operation initiated by a human operator. In one example, generating the second ECG template includes generating the second ECG template during a baselining operation initiated by the user.

In one example, generating the second ECG template includes generating the second ECG template during a baselining operation and the detection component is further configured to provide a notification regarding the baselining operation prior to generating the second ECG template. In this example, the notification may include at least one of an audible alarm, a spoken warning, a visual alert, a tactile alert, and a signal sent to a remote server.

In one example, the detection component is configured to generate at least one ECG template of the first and second ECG templates by determining numerical coefficients of one or more matched filters based on analysis of an identified ECG signal corresponding to the at least one ECG template. In this example, the detection component may be configured to determine whether the patient is experiencing a cardiac event based in part by filtering a signal corresponding to the ECG signal with at least one of the one or more matched filters.

In one example, the detection component is configured to read a parameter that specifies a delay between generation of the first ECG template and generation of the second ECG template and to generate the second ECG template after expiration of the delay. In this example, the delay may include at least one week.

In one example, the detection component is configured to compare the first ECG template to the second ECG template and to discard the second ECG template responsive the second ECG template deviating from the first ECG template by a threshold measurement. In one example, generating the second ECG template includes generating the second ECG template responsive to at least one of input by the patient and expiration of a predetermined period of time since generation of the first ECG template.

In one example, the detection component is configured to associate the first ECG template with a first patient, to associate the second ECG template with a second patient, and to identify the at least one of the first ECG template and the second ECG template based on a configurable parameter. In one example, the detection component is configured to associate the first ECG template with a first patient, associate the second ECG template with a second patient, and to identify the at least one of the first ECG template and the second ECG template based on an automatic determination of an identity of a patient as either the first or second patient from the patient's ECG signal.

In one example, the medical further includes a motion detector to detect and record historical information relating to a patient's movement, wherein the detection component is configured to identify the at least one of the first ECG template and the second ECG template based on the historical information relating to the patient's movement. In this example, the detection component may be configured to calculate an activity score based on the historical information relating to the patient's movement, and where the activity score is below an activity threshold, to identify the first ECG template as the at least one of the first ECG template and the second ECG template. In addition, the detection component may be configured to identify, where the activity score is above the activity threshold, the second ECG template as the at least one of the first ECG template and the second ECG template.

In one example, the medical device further includes at least one antenna and the detection component is configured to transmit the at least one of the first ECG template and the second ECG template to an external system. In one example, the medical device further includes at least one antenna and the detection component is configured to receive, from an external system, one or more of the first ECG template and the second ECG template.

In one example, the medical device includes at least two electrode pairs and wherein determining whether the patient is experiencing the cardiac event includes comparing each pair of signals from the at least two electrode pairs with either the first ECG template or the second ECG template using one or more matched filters. In this example, comparing may include performing a signal operation based on the one or more matched filters on each pair of signals from the at least two electrode pairs and either the first ECG template or the second ECG template. The signal operation may include a convolution operation on a signal representation of a pair of signals and either the first ECG template or the second ECG template. In addition, the at least two electrode pairs may include a front to back pair and a side to side pair.

In one example, the detection component is configured to determine whether the cardiac event is a treatable arrhythmia or an untreatable arrhythmia by performing a morphology analysis of the ECG signal with respect to the at least one of the first ECG template and the second ECG template. In this example, the morphology analysis may include detecting a QRS complex in the ECG signal, and where the QRS complex is detected, determining that the cardiac event is an untreatable arrhythmia. In another example, detecting the QRS complex may include performing a convolution operation on a signal representation of the ECG signal and a corresponding signal representation of at least one of the first and second ECG signals to determine whether one or more characteristics in the ECG signal indicate either presence or absence of the QRS complex. In addition, the treatable arrhythmia may include either ventricular tachycardia or ventricular fibrillation and/or the untreatable arrhythmia may include supraventricular tachycardia.

In one example, the medical device includes one of a wearable defibrillator and an automated external defibrillator. In one example, the cardiac event includes at least one of premature ventricular contraction (PVC), ventricular fibrillation (VF), ventricular tachycardia (VT), and supraventricular tachycardia (SVT).

Still other aspects and advantages of the examples disclosed herein are discussed in detail below. Moreover, it is to be understood that both the foregoing information and the following detailed description are merely illustrative examples of various aspects, and are intended to provide an overview or framework for understanding the nature and character of the claimed subject matter. Any example disclosed herein may be combined with any other example. References to "an example," "some examples," "an alternate example," "various examples," "one example," "at least one example," "this and other examples" or the like are not necessarily mutually exclusive and are intended to indicate that a particular feature, structure, or characteristic described in connection with the example may be included in at least one example. The appearances of such terms herein are not necessarily all referring to the same example.

Furthermore, in the event of inconsistent usages of terms between this document and documents incorporated herein by reference, the term usage in the incorporated references is supplementary to that of this document; for irreconcilable inconsistencies, the term usage in this document controls. In addition, the accompanying drawings are included to provide illustration and a further understanding of the various aspects and examples, and are incorporated in and constitute a part of this specification. The drawings, together with the remainder of the specification, serve to explain principles and operations of the described and claimed aspects and examples.

BRIEF DESCRIPTION OF DRAWINGS

The accompanying drawings are not intended to be drawn to scale. In the drawings, components that are identical or nearly identical may be represented by a like numeral. For purposes of clarity, not every component is labeled in every drawing. In the drawings:

FIG. 7 is a flow diagram of one example baselining process;

FIG. 8 is a flow diagram of one example patient monitoring process;

FIG. 9 is a flow diagram of one example ECG template selection process;

FIG. 10 is a flow diagram of another example ECG template selection process.

DETAILED DESCRIPTION

Figure 1:
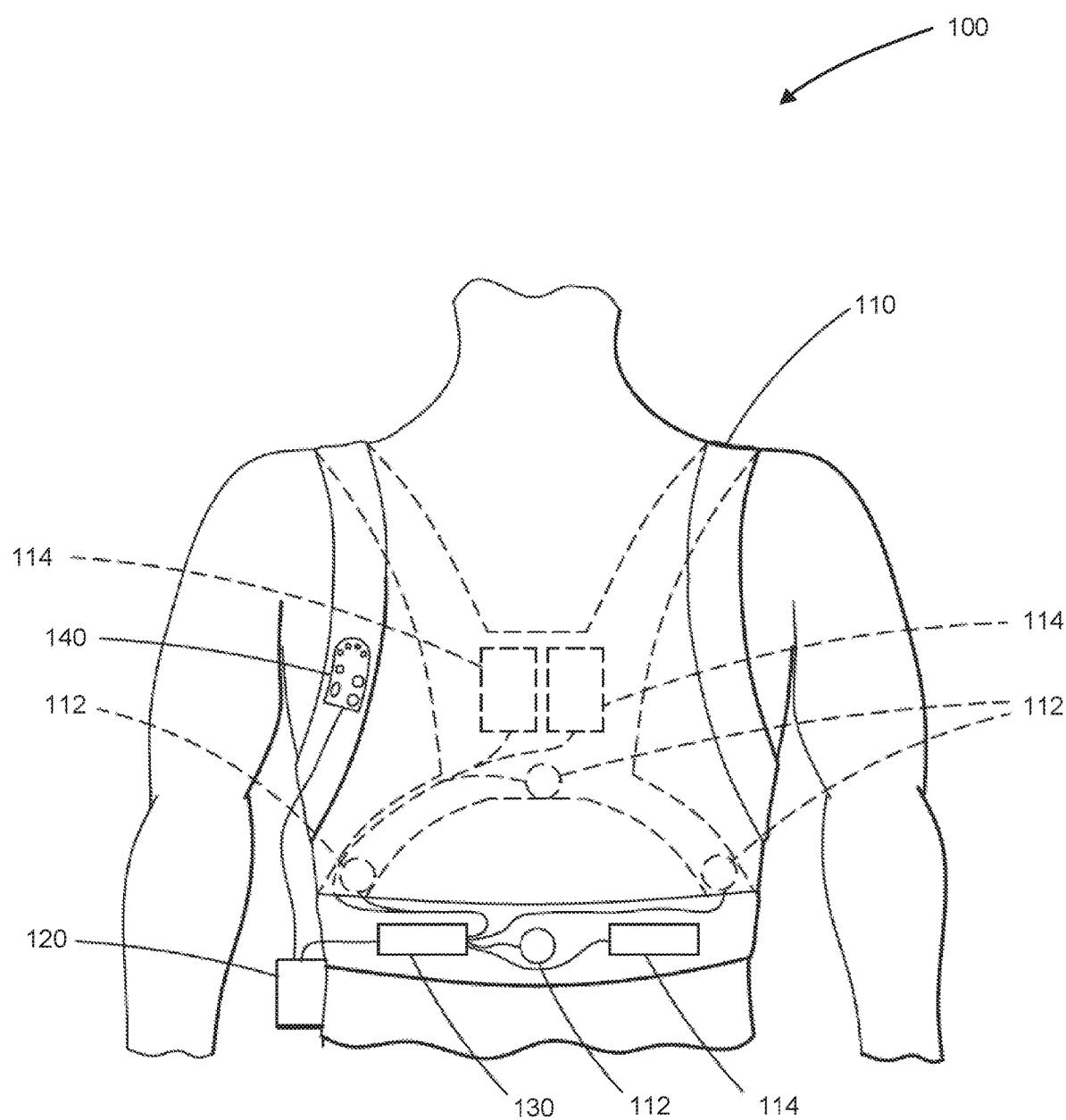
FIG. 1 is an illustration of one example of a wearable medical device.

Medical devices in accord with various examples disclosed herein monitor a patient for cardiac events including, for example, ventricular tachycardia, ventricular fibrillation, and supraventricular tachycardia. For instance, according to some examples, a medical device includes a detection component configured to generate an ECG template for a patient and determine whether the patient is experiencing a cardiac event by comparing an ECG signal of the patient with the ECG template. In some examples, the medical device generates multiple ECG templates and/or updates one or more ECG templates as appropriate for the patient. For example, the medical device may generate an ECG template for each state of the patient (e.g., a resting stating and an active state) and employ the appropriate ECG template based on a current state of the patient. In addition, the medical device may revise templates as the sinus rhythm of the patient changes over time because of, for example, changing exercise habits. For example, an ECG template as used herein can account for deviations from typical ECG signal (PQRST points), e.g., including an occurrence of premature ventricular contraction (PVC) and/or other non-standard ECG information.

Medical devices disclosed herein may be invasive or non-invasive. For example, medical devices disclosed herein may be monitoring devices (e.g., configured to monitor a cardiac signal of a patient) with or without an associated treatment component. Non-invasive devices as described herein are in contrast to invasive devices such as implantable medical devices (e.g., implantable defibrillators). For example, a non-invasive medical device as disclosed herein can include an automated external defibrillator (AED). Such AEDs are capable of monitoring cardiac rhythms, determining when a defibrillating shock is needed, and administering the shock either automatically or under the control of a trained rescuer (e.g., an EMT or other medically trained personnel). The AED may also be configured to provide cardiopulmonary resuscitation (CPR) counseling. Such an AED is available from ZOLL Medical Corporation of Chelmsford, Mass.

The non-invasive medical device as disclosed herein may be ambulatory devices that are capable of and designed for moving with the patient as the patient goes about their daily routine. For example, a non-invasive medical device as disclosed herein can be ambulatory and bodily-attached such as the LifeVest® wearable cardioverter defibrillator available from ZOLL Medical Corporation of Pittsburgh, Pa.

The examples of the methods and apparatuses discussed herein are not limited in application to the details of construction and the arrangement of components set forth in the following description or illustrated in the accompanying drawings. The methods and apparatuses are capable of implementation in other examples and of being practiced or of being carried out in various ways. Examples of specific implementations are provided herein for illustrative purposes only and are not intended to be limiting. In particular, acts, elements and features discussed in connection with any one or more examples are not intended to be excluded from a similar role in any other examples.

Also, the phraseology and terminology used herein is for the purpose of description and should not be regarded as limiting. Any references to examples or elements or acts of the systems and methods herein referred to in the singular may also embrace examples including a plurality of these elements, and any references in plural to any example or element or act herein may also embrace examples including only a single element. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms.

Example Wearable Medical Device

In one example, the medical device is a wearable medical device that includes a garment (e.g., a vest or belt) that is worn by the patient. The wearable medical device monitors the patient's ECG with sensing electrodes, detects life-threatening arrhythmias, and delivers a cardioverting or defibrillating shock through therapy pads if treatment is necessary. FIG. 1 illustrates an example wearable medical device, such as a LifeVest® wearable cardioverter defibrillator available from ZOLL Medical Corporation of Chelmsford, Mass. As shown, the wearable medical device 100 includes a harness 110 having a pair of shoulder straps and a belt that is worn about the torso of a patient. The wearable medical device 100 includes a plurality of ECG sensing electrodes 112 that are attached to the harness 110 at various positions about the patient's body and electrically coupled to a sensor interface of the medical device controller 120 via a connection pod 130. The plurality of ECG sensing electrodes 112, which may be dry-sensing capacitance electrodes, are coupled to the medical device controller 120 to monitor the cardiac function of the patient and generally include a front-back (FB) pair of ECG sensing electrodes and a side-side (SS) pair of ECG sensing electrodes. Additional ECG sensing electrodes may be provided, and the plurality of ECG sensing electrodes 112 may be disposed at varying locations about the patient's body.

The wearable medical device 100 also includes a plurality of therapy electrodes 114 that are electrically coupled to the medical device controller 120 via the connection pod 130 and which are configured to deliver one or more therapeutic defibrillating shocks to the body of the patient, if it is determined that such treatment is warranted. The connection pod 130 electrically couples the plurality of ECG sensing electrodes 112 and the plurality of therapy electrodes 114 to the medical device controller 120, and may include electronic circuitry. The connection pod 130 may also include other electronic circuitry, such as a motion sensor or accelerometer through which patient activity may be monitored. It is appreciated that the wearable medical device 100 may be a monitoring only device and omit the therapy delivery capabilities and associated components including, for example, the therapy electrodes 114. In other examples, the wearable medical device 100 is a convertible wearable medical device that is capable of switching between a monitoring only wearable medical device and a wearable treatment device. In these examples, the various treatment components may be packaged into various modules that can be attached or removed from the wearable medical device as needed.

As shown in FIG. 1, the wearable medical device 100 may include a user interface pod 140 that is electrically coupled to, or integrated in with, the user interface of the medical device controller 120. The user interface pod 140 can be attached to the patient's clothing or to the harness 110, for example, via a clip (not shown) that is attached to a portion of the interface pod 140. Alternatively, the user interface pod 140 may simply be held in a person's hand. For example, such a user interface pod 140 can be a smartwatch or a smartphone. In some examples, the user interface pod 140 may communicate wirelessly with the user interface of the medical device controller 120, for example, using a Bluetooth®, Wireless USB, ZigBee, Wireless Ethernet, GSM, or other type of communication interface.

The user interface pod 140 includes a number of buttons by which the patient, or a bystander can communicate with the medical device controller 120, and a speaker by which the medical device controller 120 may communicate with the patient or the bystander. For example, where the medical device controller 120 determines that the patient is experiencing cardiac arrhythmia, the medical device controller 120 may issue an audible alarm via a speaker on the medical device controller 120 or the user interface pod 140 alerting the patient and any bystanders to the patient's medical condition. The medical device controller 120 may also instruct the patient to press and hold one or more buttons on the user interface of the medical device controller 120 or on the user interface pod 140 to indicate that the patient is conscious, thereby instructing the medical device controller 120 to withhold the delivery of one or more therapeutic defibrillating shocks. If the patient does not respond, the device may determine that the patient is unconscious, and proceed with the treatment sequence, culminating in the delivery of one or more defibrillating shocks to the body of the patient. In implementations, prior to delivering the shock, conductive gel may be deployed to reduce an impedance seen by the therapy electrodes during the delivery of the shock.

Figure 2B:
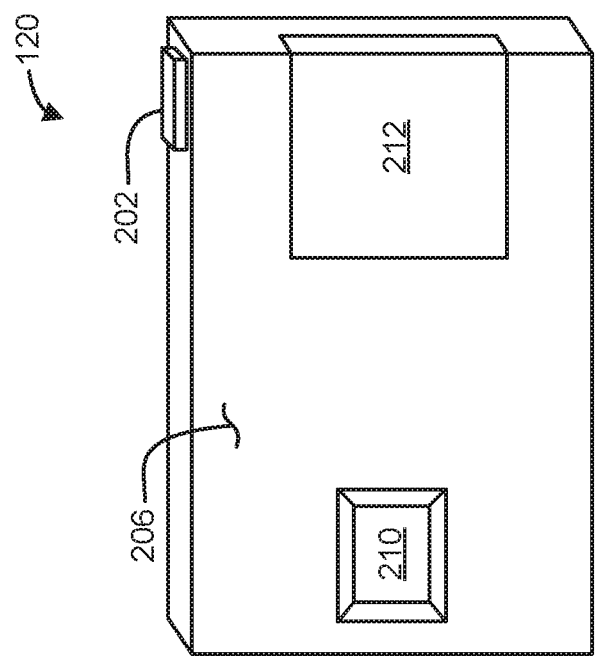
FIGS. 2A-2B are illustrations of one example of a medical device controller for a medical device.
Figure 2A:
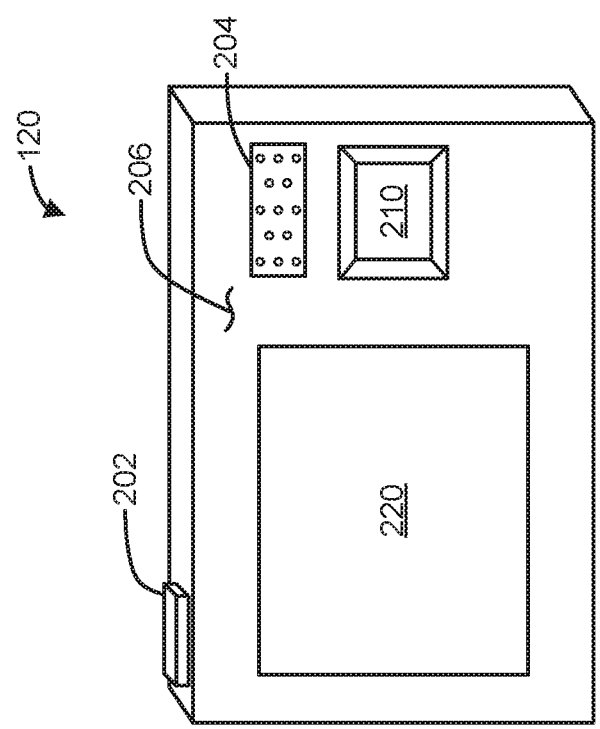

In another example, the functionality of the user interface pod 140 is integrated into the housing of the medical device controller 120. FIGS. 2A-2B illustrate such an example of the medical device controller 120. The controller 120 may be powered by a rechargeable battery 212. The rechargeable battery 212 may be removable from a housing 206 of the medical device controller 120 to enable a patient and/or caregiver to swap a depleted (or near depleted) battery 212 for a charged battery. The medical device controller 120 includes two response buttons 210 on opposing sides of the housing 206 of the medical device controller 120. As shown in FIGS. 2A-2B, the response buttons 210 are recessed to reduce the likelihood of accidental activation (e.g., a patient falling on the response button). The medical device controller 120 also includes, in this example, a display screen 220 and a speaker 204 to enable the communication of audible and visual stimuli to the patient. It is appreciated that the response buttons 210 do not have to be placed on opposing sides of the housing as illustrated in FIGS. 2A-2B. The response buttons 210, for example, may be located adjacent to each other in the housing the ambulatory medical device controller. The adjacent placement of the response buttons 210 may make it easier for individuals with smaller hands or less dexterity to engage the response buttons. The medical device controller 120 may further include a port 202 to removably connect sensing devices (e.g., ECG sensing electrodes 112) and/or therapeutic devices (e.g., therapy electrodes 114) to the medical device controller 120.

Another example wearable medical device is the ambulatory external defibrillator described in FIG. 1 of U.S. Pat. No. 8,904,214, titled "SYSTEM AND METHOD FOR CONSERVING POWER IN A MEDICAL DEVICE," issued Dec. 2, 2014 (hereinafter the "'214 patent"), which is hereby incorporated herein by reference herein in its entirety. In at least one example, the ambulatory defibrillator 100 illustrated in FIG. 1 of the '214 patent may employ the medical device controller 120, as disclosed in the present application, as a substitute for the portable treatment controller 200 described in the '214 patent. In such an example, the ECG electrodes and therapy pads illustrated in FIG. 1 of the '214 patent may be logically and physically coupled to the medical device controller 120. While some of the examples disclosed herein are directed to wearable medical devices, the systems and methods disclosed herein may be readily applied to other medical devices including, for example, an Automated External Defibrillator (AED)

Example Medical Device for Use in a Health Care Facility Setting

Figure 3:
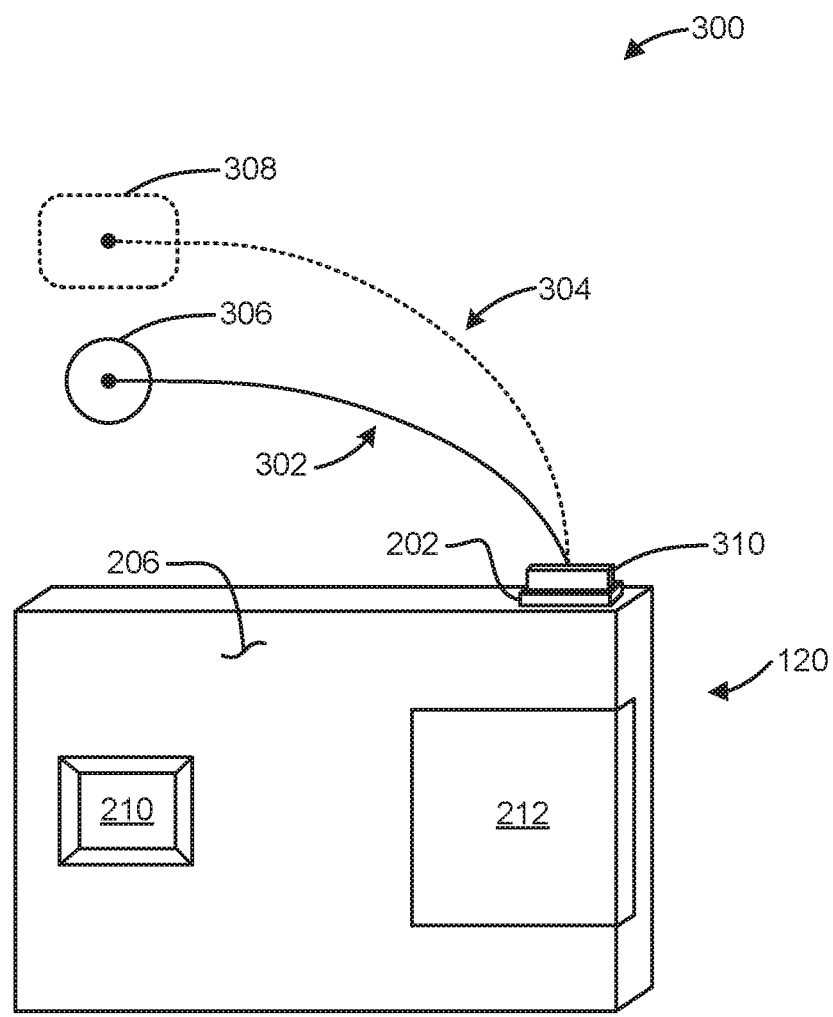
FIG. 3 shows an example medical device for monitoring and treating patients in a healthcare facility.

In some examples, the medical device for use in an inpatient context, e.g., for use with patients admitted to a health care facility, such as, a hospital. FIG. 3 illustrates an example hospital based medical device employing the medical device controller 120. The hospital based medical device may be constructed to provide cardiac monitoring and/or treatment for patients in a hospital setting who may be, for example, bedridden and/or limited-mobility patients. As illustrated in FIG. 3, the hospital based medical device 300 includes the medical device controller 120 and a sensing component 302. The sensing component 302 includes a connector 310 constructed to removably couple to the port 202 of the medical device controller 120. The sensing component 302 may detect information indicative of cardiac activity of the patient including, for example, ECG activity, tissue fluid, lung fluid, lung sounds, heart sounds, and/or patient activity. In some examples, the sensing component 302 includes one or more electrodes 306. The electrodes 306 may be stick-on adhesive electrodes constructed to attach to the patient. In some examples, the electrodes 306 may be detachable from a wire lead coupling the electrode 306 to the connector 310. Constructing the sensing component 302 to make the electrodes 306 detachable may enable the patient and/or caregiver to periodically (e.g., every 24-48 hours or more, as prescribed) replace the electrodes 306 without replacing the entire sensing component 302. For example, the electrodes 306 may be long term wear electrodes that are configured to be continuously worn by a patient for extended periods (e.g., 3 or more days).

In some examples, the hospital based medical device 300 may also include a treatment component 304 to provide treatment to the patient. The treatment component 304 may include, for example, a therapy pad 308 configured to attach to the patient. The treatment component 304 may be connected to the same connector 310 as the sensing component 302 and/or employ a separate connector that is capable of coupling to the connector 310. It is appreciated that the treatment component 304 may be integrated into the sensing component 302 in a combined sensing-treatment component. The combined sensing-treatment component may include an electrode with integrated sensing and treatment delivery capabilities as described in the '214 patent.

Example Monitoring Medical Device

In some examples, the medical device may be a patient monitoring device such as a mobile cardiac telemetry (MCT) monitor. For example, such a patient monitoring device may be configured to monitor one or more of a patient's physiological parameters. For example, a patient monitor may include a cardiac monitor for monitoring a patient's cardiac information. Such cardiac information can include, without limitation, heart rate, ECG data, heart sounds data from an acoustic sensor, and other cardiac data. In addition to cardiac monitoring, the patient monitor may perform monitoring of other relevant patient parameters, including glucose levels, blood oxygen levels, lung fluids, lung sounds, and blood pressure.

An example cardiac monitoring medical device (e.g., a cardiac monitor) may be similar to the wearable medical device 100 and/or the hospital based medical device 300 described above with reference to FIGS. 1-3 and omit, for example, the therapy electrodes 114 and/or the therapy pad 308. In some implementations, the cardiac monitor is capable of and designed for being worn by a patient who is at risk of developing cardiac problems, but who does not yet meet criteria to be outfitted with a medical device that includes a treatment component (e.g., a defibrillator).

In some implementations, the patient can interact with a user interface of the cardiac monitor to identify one or more patient symptoms. The user interface may include a touchscreen that provides a drop down menu or check list which, in turn, allows the patient to select a particular symptom from a list of alternatives. Options for patient systems can include one or more of: feeling a skipped beat, shortness of breath, light headedness, racing heart rate, fatigue, fainting, chest discomfort, weakness, dizziness, and/or giddiness. In addition, the patient can select a level of activity (e.g., light activity, moderate activity, rigorous activity, etc.) that he or she was performing when the symptom occurred. In some implementations, in response to the selection by the patient, the cardiac monitor can cause a portion of patient physiological information (e.g., in the form of a cardiac signal) to be captured for a length of time that is based on when the symptom was experienced. For example, the cardiac monitor can cause a portion of an ECG signal of the patient to be captured. The portion of the ECG signal that is captured can be associated with the reported symptom and patient information.

Thus, the cardiac monitor may be prescribed so that continuous and/or event-based data can be sent from the cardiac monitor to a remote server. A caregiver can access the data from the remote server and determine whether the patient is experiencing or has experienced a cardiac problem. In some implementations, after determining that the patient is experiencing a cardiac problem, the caregiver may instruct the patient to begin wearing a medical device with treatment capabilities.

Example Medical Device Controller

Figure 4:
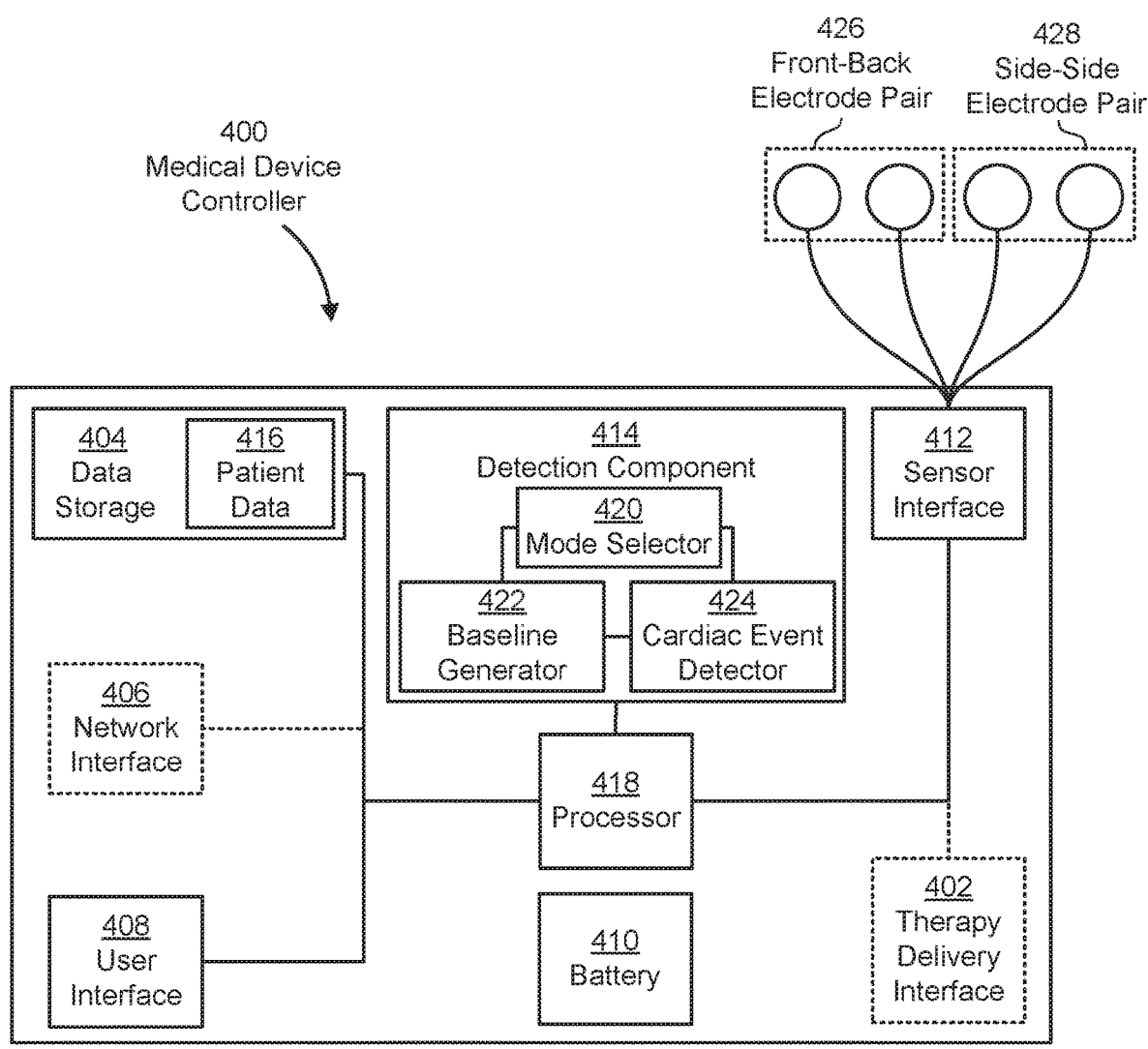
FIG. 4 is a functional schematic of one example of a medical device controller.

FIG. 4 illustrates a medical device controller 400 that is configured to monitor the cardiac activity of a patient and/or provide therapy to the patient as needed. The medical device controller 400 may, for example, be configured for use in a wearable medical device (e.g., medical device controller 120). The medical device controller 400 has a variety of potential applications and is well suited to devices that notify external entities of one or more events of interest (e.g., cardiac events). Examples of devices to which the medical device controller 400 is well suited include critical care medical devices, such as a wearable ambulatory external defibrillator, an in-hospital defibrillator, an AED, or a mechanical chest compression device, such as the Autopulse® system from ZOLL Medical Corporation of Chelmsford, Mass.

As shown in FIG. 4, the medical device controller 400 includes a processor 418, a sensor interface 412, a detection component 414, a therapy delivery interface 402, data storage 404 including patient data 416, a communication network interface 406, a user interface 408, and a battery 410. The detection component 414 includes a mode selector 420, a baseline generator 422, and a cardiac event detector 424. The sensor interface 412, as illustrated, is coupled to electrodes including a front-back (FB) electrode pair 426 and a side-side (SS) electrode pair 428. It is appreciated that the electrode configuration and/or the number of electrodes may be changed to best suit the particular application.

In some examples, the battery 410 is a rechargeable battery that provides electrical power to other components within the medical device. The particular capacity and type of battery (e.g., lithium ion, nickel-cadmium, or nickel-metal hydride) employed may vary based on the desired runtime between charges of the medical device and the power consumption of the components. For example, the battery 410 may be selected to provide a minimum runtime between charges of 44 hours. In this example, a suitable battery may include a 3 cell 4200 mAh lithium ion battery pack. It is appreciated that various mechanisms may be employed to removably secure the battery 410 to the medical device controller 400 including, for example, a latching mechanism.

According to the example illustrated in FIG. 4, the processor 418 is coupled to the sensor interface 412, the therapy delivery interface 402, the data storage 404, the network interface 406, and the user interface 408. The processor 418 performs a series of instructions that result in manipulated data which are stored in and retrieved from the data storage 404. According to a variety of examples, the processor 418 is a commercially available processor such as a processor manufactured by Texas Instruments, Intel, AMD, Sun, IBM, Motorola, Freescale, and ARM Holdings. However, the processor 418 may be any type of processor, multiprocessor or controller, whether commercially available or specially manufactured. For instance, according to one example, the processor 418 may include a power conserving processor arrangement such as described in the '214 patent. In another example, the processor 418 is an Intel® PXA270.

In addition, in some examples, the processor 418 may be configured to execute a conventional operating system. The operating system may provide platform services to application software, such as some examples of the detection component 414 which is discussed further below. These platform services may include inter-process and network communication, file system management and standard database manipulation. One or more of many operating systems may be used, and examples are not limited to any particular operating system or operating system characteristic. For instance, operating systems can include a Windows based operating system, OSX, or other operating systems. For instance, in some examples, the processor 418 may be configured to execute a real-time operating system (RTOS), such as RTLinux, or a non-real time operating system, such as BSD or GNU/Linux.

In some examples, the detection component 414 is configured to monitor the cardiac activity of the patient and identify cardiac events experienced by the patient. The detection component 414 is described in greater detail below with reference to FIGS. 5-10. The detection component 414 may be implemented using hardware or a combination of hardware and software. For instance, in one example, the detection component 414 is implemented as a software component that is stored within the data storage 412 and executed by the processor 418. In this example, the instructions included in the detection component 414 program the processor 418 to monitor the cardiac activity of the patient and identify cardiac events experienced by the patient. In other examples, the detection component 414 may be an application-specific integrated circuit (ASIC) that is coupled to the processor 418. Thus, examples of detection component 414 are not limited to a particular hardware or software implementation.

In some examples, the components disclosed herein, such as the detection component 414, may read parameters that affect the functions performed by the components. These parameters may be physically stored in any form of suitable memory including volatile memory, such as RAM, or non-volatile memory, such as a flash memory or magnetic hard drive. In addition, the parameters may be logically stored in a propriety data structure, such as a database or file defined by a user mode application, or in a commonly shared data structure, such as an application registry that is defined by an operating system. In addition, some examples provide for both system and user interfaces, as may be implemented using the user interface 408, that allow external entities to modify the parameters and thereby configure the behavior of the components.

The data storage 404 includes a computer readable and writeable nonvolatile data storage medium configured to store non-transitory instructions and data. In addition, the data storage 404 includes processor memory that stores data during operation of the processor 418. In some examples, the processor memory includes a relatively high performance, volatile, random access memory such as dynamic random access memory (DRAM), static memory (SRAM) or synchronous DRAM. However, the processor memory may include any device for storing data, such as a non-volatile memory, with sufficient throughput and storage capacity to support the functions described herein. According to several examples, the processor 418 causes data to be read from the nonvolatile data storage medium into the processor memory prior to processing the data. In these examples, the processor 418 copies the data from the processor memory to the non-volatile storage medium after processing is complete. A variety of components may manage data movement between the non-volatile storage medium and the processor memory and examples are not limited to particular data management components. Further, examples are not limited to a particular memory, memory system or data storage system.

The instructions stored on the data storage 404 may include executable programs or other code that can be executed by the processor 418. The instructions may be persistently stored as encoded signals, and the instructions may cause the processor 418 to perform the functions described herein. The data storage 404 also may include information that is recorded, on or in, the medium, and this information may be processed by the processor 418 during execution of instructions. The medium may, for example, be optical disk, magnetic disk or flash memory, among others, and may be permanently affixed to, or removable from, the medical device controller 400.

In some examples, the patient data 416 includes ECG templates associated with one or more patients. The ECG templates may be stored as, for example, a series of matched filter coefficients. The stored matched filter coefficients may be employed during monitoring by, for example, a matched filter to compare the received ECG signal from the patient with the ECG template associated with the patient. As illustrated in FIG. 4, the detection component 414 and the patient data 416 are separate components. However, in other examples, the detection component 414 and the patient data 416 may be combined into a single component or re-organized so that a portion of the data included in the detection component 414, such as executable code that causes the processor 418 to generate ECG templates and monitor any cardiac events experienced by the patient, resides in the patient data 416, or vice versa. Such variations in these and the other components illustrated in FIG. 4 are intended to be within the scope of the examples disclosed herein.

The patient data 416 may be stored in any logical construction capable of storing information on a computer readable medium including, among other structures, flat files, indexed files, hierarchical databases, relational databases, or object oriented databases. These data structures may be specifically configured to conserve storage space or increase data exchange performance. In addition, various examples organize the patient data 416 into particularized and, in some cases, unique structures to perform the functions disclosed herein. In these examples, the data structures are sized and arranged to store values for particular types of data, such as integers, floating point numbers, character strings, arrays, linked lists, and the like.

As shown in FIG. 4, the medical device controller 400 includes several system interface components 402, 406, and 412. Each of these system interface components is configured to exchange, i.e. send or receive, data with one or more specialized devices that may be located within the housing of the medical device controller 400 or elsewhere. The components used by the interfaces 402, 406, and 412 may include hardware components, software components or a combination of both. Within each interface, these components physically and logically couple the medical device controller 400 to the specialized devices. This physical and logical coupling enables the medical device controller 400 to communicate with and, in some instances, power or control the operation of the specialized devices. These specialized devices may include physiological sensors, therapy delivery devices, and computer networking devices.

According to various examples, the hardware and software components of the interfaces 402, 406, and 412 implement a variety of coupling and communication techniques. In some examples, the interfaces 402, 406, and 412 use leads, cables or other wired connectors as conduits to exchange data between the medical device controller 400 and specialized devices. In other examples, the interfaces 402, 406, and 412 communicate with specialized devices using wireless technologies such as radio frequency or infrared technology. The software components included in the interfaces 402, 406, and 412 enable the processor 418 to communicate with specialized devices. These software components may include elements such as objects, executable code, and populated data structures. Together, these software components provide software interfaces through which the processor 418 can exchange information with specialized devices. Moreover, in at least some examples where one or more specialized devices communicate using analog signals, the interfaces 402, 406, and 412 further include components configured to convert analog information into digital information, and vice versa, to enable the processor 418 to communicate with specialized devices.

As discussed above, the system interface components 402, 406, and 412 shown in the example of FIG. 4 support different types of specialized devices. For instance, the components of the sensor interface 412 couple the processor 418 to one or more physiological sensors such as a body temperature sensors, respiration monitors, and electrocardiogram (ECG) sensing electrodes, one or more environmental sensors such as atmospheric thermometers, airflow sensors, video sensors, audio sensors, accelerometers, GPS locators, and hygrometers, or one or more motion detection sensors such as altimeters, accelerometers, and gyroscopes. In these examples, the sensors may include sensors with varying sampling rates, including wireless sensors. The sensor interface 412, as illustrated, is coupled to four ECG sensing electrodes that form a front-back (FB) electrode pair 426 and a side-side (SS) electrode pair 428. The sensor interface may include various circuitry to amplify the ECG signal detected by the electrodes, condition the received ECG signal, and/or digitize the ECG signals as described in U.S. Pat. No. 8,600,486, titled "METHOD OF DETECTING CLIPPING IN A WEARABLE AMBULATORY MEDICAL DEVICE" and issued on Dec. 3, 2013 (hereinafter the "'486 patent"), which is hereby incorporated herein by reference in its entirety. It is appreciated that the particular number of ECG sensing electrodes coupled to the sensor interface 412 and/or the pairing of the ECG sensing electrodes may vary based on the specific implementation.

In some examples, the components of the therapy delivery interface 402 couple one or more therapy delivery devices, such as capacitors, defibrillator electrodes, pacing electrodes or mechanical chest compression devices, to the processor 418. It is appreciated that the functionality of the therapy delivery interface 402 may be incorporated into the sensor interface 412 to form a single interface coupled to the processor 418. In addition, the components of the network interface 406 couple the processor 418 to a computer network via a networking device, such as a bridge, router or hub. According to a variety of examples, the network interface 406 supports a variety of standards and protocols, examples of which include USB (via, for example, a dongle to a computer), TCP/IP, Ethernet, Wireless Ethernet, Bluetooth, ZigBee, M-Bus, CAN-bus, IP, IPV6, UDP, DTN, HTTP, HTTPS, FTP, SNMP, CDMA, NMEA and GSM. It is appreciated that the network interface 406 of medical device controller 400 may enable communication between other medical device controllers within a certain range.

To ensure data transfer is secure, in some examples, the medical device controller 400 can transmit data via the network interface 406 using a variety of security measures including, for example, TLS, SSL or VPN. In other examples, the network interface 406 includes both a physical interface configured for wireless communication and a physical interface configured for wired communication. According to various examples, the network interface 406 enables communication between the medical device controller 400 and a variety of personal electronic devices including, for example, computer enabled glasses, wristwatches, earpieces, and phones.

In one example, the network interface 406 is also capable of transmitting and/or receiving information to assist in monitoring the cardiac function of the patient. This may be accomplished through one or more antennas integrated with or coupled to the network interface 406, and consequently coupled to the processor 418. For example, the one or more antennas may receive information representative of the ECG template associated with the patient. The wireless signals received by the antennas may be analyzed by the processor 418 to generate an ECG template for the patient. The network interface 406 may also transmit one or more generated ECG templates to an external system. For example, the medical device may transmit the ECG template associated with a patient to a health care provider of the patient. The health care provider may provide the ECG template to one or more other medical devices employed to provide treatment to the patient.

Thus, the various system interfaces incorporated in the medical device controller 400 allow the device to interoperate with a wide variety of devices in various contexts. For instance, some examples of the medical device controller 400 are configured to perform a process of sending critical events and data to a centralized server via the network interface 406. An illustration of a process in accord with these examples is disclosed in U.S. Pat. No. 6,681,003, titled "DATA COLLECTION AND SYSTEM MANAGEMENT FOR PATIENT-WORN MEDICAL DEVICES," and issued on Jan. 20, 2004, which is hereby incorporated herein by reference in its entirety.

As illustrated in FIG. 4, the therapy delivery interface 402 is optional and may not be included in every example. For instance, an MCT monitor or other monitoring device may employ the medical device controller 400 to issue alarms but may not include a therapy delivery interface 402 to treat cardiac abnormalities. Similarly, an ambulatory defibrillator may include the medical device controller 400 to provide alarm functionality but may not include a network interface 406 where, for example, the ambulatory defibrillator is designed to rely on the user interface 408 to announce alarms.

The user interface 408 shown in FIG. 4 includes a combination of hardware and software components that allow the medical device controller 400 to communicate with an external entity, such as a patient or other user. These components may be configured to receive information from actions such as physical movement, verbal intonation, or thought processes. In addition, the components of the user interface 408 can provide information to external entities. Examples of the components that may be employed within the user interface 408 include keyboards, mouse devices, buttons, microphones, electrodes, touch screens, printing devices, display screens, and speakers. In some examples, the electrodes include an illuminating element, such as an LED. In other examples, the printing devices include printers capable of rendering visual or tactile (Braille) output.

In some examples, the user interface 408 may be configured to provide information to external entities regarding a cardiac event experienced by the patient. For example, the user interface 408 may provide an alarm indicting that the patient is experiencing an arrhythmia. In these examples, the user interface may also receive input from the patient regarding the cardiac event. For example, the user interface 408 may issue an alarm requesting the patient to interact with at least one element of the user interface 408 (e.g., push a button) to delay the administration of therapy (e.g., a defibrillating shock) and/or acknowledge the alarm.

In some examples, the detection component 414 monitors the cardiac condition of the patient. The detection component 414 may monitor the cardiac condition of the patient by generating an ECG template for the patient and comparing the ECG template with the ECG signal of the patient to identify cardiac events. For example, comparing the ECG template with the ECG signal of the patient can include filtering the incoming ECG signal through a filter comprising the ECG template as described in further detail below. In an implementation, the filtering operation can include a predetermined mathematical operation (e.g., a convolution) involving a signal representation of the ECG template and the ECG signal of the patient. The functions of the detection component 414 may be divided between a baselining mode (e.g., a "learn mode") where ECG templates are generated, and a monitoring mode where the ECG templates are compared with the ECG signal of the patient. As illustrated in FIG. 4, the baseline generator 422 performs the various processes associated with baselining mode while the cardiac event detector 424 performs the various processes associated with the monitoring mode. The mode selector 420 of the detection component 414 controls the operating mode of the medical device (e.g., whether the medical device is in a monitoring mode or a baselining mode). It is appreciated that the particular architecture shown in FIG. 4 is for illustration only and other architectures and/or modes may be employed by the detection component 414.

Example Baselining

The baseline generator 422 generates an ECG template associated with the patient. The ECG template may be indicative of a normal sinus rhythm of the patient. In some examples, the ECG template may also account for rate and morphological variations in patient populations in composing the template. For example, the ECG template can account for ectopic beats such as premature ventricular contractions (PVCs). The ECG template is employed by the cardiac event detector 424 to determine whether the patient is experiencing a cardiac event. FIG. 7 illustrates an example baselining process 700 performed by, for example, the baseline generator 422. In some examples, the baseline mode of the device can be accessed for performing the baselining. This process can be performed before active patient monitoring operation begins. As discussed below, in some implementations, the process can be repeated periodically, e.g., once every two weeks, or when prompted by an external event (e.g., user-triggered event) or an internal event (e.g., automated detection of a triggering condition).

Example triggering conditions can include, without limitation, one or more of a change in patient profile information or data (e.g., through a manual or automated remote or local download process), device or user initiated periodic or aperiodic self-tests, mechanical impact detection (e.g., when the device is subject to forces beyond a predetermined threshold), tampering of the device, assembly and/or disassembly events involving the device, excess temperature and/or moisture events, battery change events, post-shock delivery (e.g., a period of time after a shock has been delivered), an arrhythmia warning or alert event (e.g., when the patient is conscious and able to respond by pushing the response buttons), actuation of the response buttons (e.g., actuation of the buttons in a predetermined manner), changes in and/or tampering of gel deployment mechanism, detected excessive cabling and/or device strains, error conditions thrown by monitor software, and monitor software updates.

During the ECG baseline sequence, the patient's normal rhythm can be recorded and analyzed as described below. A user interface can provide messages and interface with a user (either the patient or a caregiver) to allow the recording of the ECG data. When the user interface receives notification that the baseline process has successfully completed, the user can be notified by a display and/or an alarm.

In an example, the baselining process can include the acts of recording the patient ECG signal 702, determining a composite QRST waveform based on the recorded patient ECG signal 704, and identifying filter parameters based on the QRST waveform 706 as the ECG template. The baselining process 700 may also include transmitting the filter parameters to an external system 708 (e.g., a computer system of a health care provider associated with the patient) for storage, review, and/or analysis. For example, a caregiver may remotely accept or reject a recorded ECG template without requiring that the patient be physically present in the caregiver's office.

In act 702, the medical device records the ECG signal of the patient. As discussed above, the medical device may include various sensing electrodes placed around the body of the patient. In some examples, the medical device includes multiple pairs of ECG electrodes (e.g., a front-back electrode pair and a side-side electrode pair). In these examples, the medical device may record the ECG signal received from both pairs simultaneously. The recorded ECG signal of the patient from which the ECG template is derived may be stored locally in, for example, the patient data 416 of the medical device controller 400. It is appreciated that the duration of the ECG signal recording may vary based on the particular application. In some examples, the duration of the ECG signal recorded is between one minute and five minutes. In some examples, the duration of the ECG signal recorded for deriving an ECG template is at least 10 seconds. In an implementation, the baseline generator 422 can include a morphology analyzer for detecting QRS complexes in the recorded ECG signal during the derivation of the ECG template. For example, the ECG template can be obtained as a complex composite by, e.g., combining averaged ECG signals from side-to-side electrodes and front-to-back electrodes. For example, such a composite template can have a duration in a range from 0.5 to 2 seconds. In some implementations, however, the composite template can be configured to have durations of less than 0.5 seconds or more than 2 seconds. The ECG template can be obtained such that the QRS complex resides in a middle of the ECG template.

In act 704, the medical device determines, e.g., an average of the QRST waveforms within the recorded ECG signal. A person of ordinary skill in the art, given the benefit of this disclosure, can appreciate that rather than an average, any other method for determining a composite representing the recorded ECG signal may be used. For example, the recorded ECG signal of the patient may include two minutes of ECG data of a patient with a normal heart rate between 60 and 100 beats per minute (bpm). In this example, the recorded ECG data may include between 120-200 individual QRST waveforms associated with the 120-200 heartbeats of the patient over the two minute period. Each of the QRST waveforms may be identified and composed together (e.g., averaged) to form a QRST waveform template representative of a normal sinus rhythm of the patient.

Once the QRST waveform template is generated by the baseline generator 422, the QRST waveform template may be compared with the QRST waveforms received from the patient to facilitate the identification of cardiac events. An example method of comparing a known signal shape (e.g., the QRST waveform template) with another signal (e.g., the incoming ECG signal of the patient) is by constructing a matched filter and filtering the signal with the matched filter. Matched filters may include, for example, filters with an impulse response similar to a conjugate time-reversed version of the template signal. Filtering a signal by a matched filter may be equivalent to convolving the signal with a conjugate time-reversed version of the template signal in the time-domain and/or multiplying a frequency domain representation of the signal with the frequency domain representation of the template signal. The output of a matched filter is a correlation between the signal received by the matched filter and the template associated with the matched filter. Employing a matched filter may be an advantageous comparison method because the correlation values provided by matched filters are generally very robust to additive noise in the received signal including, for example, Additive White Gaussian Noise (AWGN). Matched filters may be implemented, for example, as a finite impulse response (FIR) filter. These FIR filters may be represented by a series of filter coefficients (e.g., between 100-200 numerical coefficients) that create a filter with the desired impulse response. Accordingly, in act 706, the medical device generates the appropriate filter coefficients based on the QRST waveform template to form the matched filter.

In some examples, the baseline generator 422 may transmit the filter coefficients associated with the matched filter to an external system as illustrated by act 708. For example, the filter coefficients may be provided to a computer system of a health care provider associated with the patient. The computer system of the health care provider may wirelessly transmit the filter coefficients to medical devices employed to provide treatment to the patient.

It is appreciated that other methods may be employed to generate the template, and the techniques described herein are not to be limited to the specific examples described here. For example, the baseline generator may receive the filter coefficients descriptive of the matched filter from an external system. In addition, multiple ECG templates may be generated and/or other patient related information may be recorded while the patient ECG information is recorded. For example, the baseline generator 422 may record the activity level of the patient in act 702 while the ECG signal of the patient is recorded. The activity level may be monitored by recording the movement of the patient detected by an accelerometer (e.g., coupled to the sensor interface 412). In this example, an activity score may be derived from the detected activity level during ECG recording and be associated with the generated ECG template. The activity score associated with the ECG template may be used in the cardiac monitoring processes performed by the cardiac event detector 424 to select an appropriate ECG template to monitor the patient as described below with reference to FIGS. 8 and 9.

In some examples, the ECG template may be associated with additional patient parameters recorded and stored along with the ECG template. In some situations, such additional information can provide details regarding the circumstances in which the ECG template was recorded. For example, if the ECG template recording was prompted by an uptick in patient activity, an average heart rate during the baselining period and/or during a period of time preceding the baselining or the prompt to perform the baselining, e.g., one week before, may be recorded and stored with the ECG template.

Example Cardiac Event Detection Circuitry

The cardiac detector 424 monitors the ECG signal of the patient to detect cardiac events experienced by the patient. The cardiac detector 424 may also determine which particular cardiac event the patient is currently experiencing including, for example, ventricular fibrillation, ventricular tachycardia, and supraventricular tachycardia. In some examples, the cardiac detector 424 employs one or more ECG templates generated by the baseline generator 422 to compare with the ECG signal of the patient. As briefly described above, the comparison between the ECG signal of the patient and the ECG template may be performed by employing one or more matched filters. The cardiac detector 424 may analyze the phase and/or magnitude of the matched filter output (e.g., the correlation signal) to identify cardiac events. For example, the cardiac detector 424 may determine that the patient is not experiencing a cardiac event originating in a heart ventricle responsive to the peak magnitude of the correlation signal occurring at, or near, a zero phase crossing of the correlation signal. As the peak in the correlation magnitude moves away from the zero phase crossing point (e.g., greater than 10-20°), the cardiac detector 424 may determine that a cardiac event originating in a heart ventricle is present including, for example, ventricular tachycardia or ventricular fibrillation. The cardiac detector 424 may further analyze the heart rate of the patient to identify cardiac events originating in other areas of the heart (e.g., in an atrium).

Figure 5:
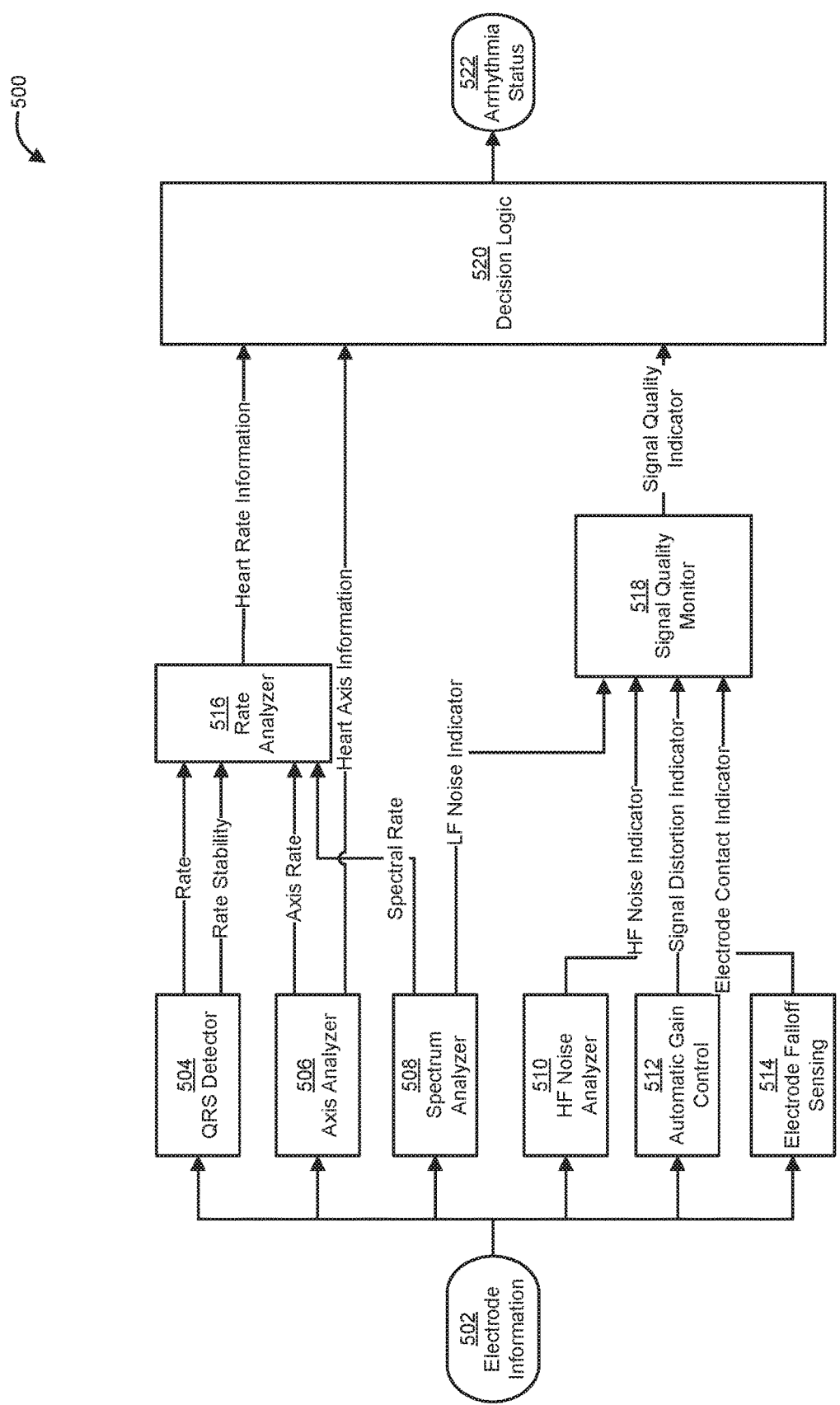
FIG. 5 is a block diagram of one example of a cardiac event detector.

FIG. 5 illustrates a block diagram of an example cardiac event detector 500 for detecting cardiac events experienced by the patient by various morphology analysis techniques (e.g., cardiac event detector 424). The cardiac event detector 500 receives electrode information 502 from the various electrodes in the medical device. The electrode information 502 may include information from, for example, a front-back electrode pair (e.g., front-back electrode pair 426) and a side-side electrode pair (e.g., side-side electrode pair 428). The cardiac event detector 500 provides an arrhythmia status 522 indicating whether the patient is experiencing an arrhythmia. The arrhythmia status 522 may also include an indication of the particular type of arrhythmia the patient is experiencing including, for example, an indication of whether the patient is experiencing supraventricular tachycardia, ventricular tachycardia, or ventricular fibrillation. It is appreciated that the various blocks included within the cardiac event detector 500 may be implemented in hardware, software, or a combination of hardware and software. For example, the electrode information 502 may include a digitized ECG signal of the patient and each of the blocks may be function blocks executed by a Digital-Signal-Processor (DSP).

The high frequency (HF) noise analyzer block 510, automatic gain control block 512, and electrode falloff sensing block 514 each generate information indicative of the quality of the ECG information being received. For example, the HF noise analyzer block 510 identifies high frequency noise in the ECG information and provides an HF noise indicator illustrative of the level of high frequency noise detected. The automatic gain control block 512 may control the gain of one or more gain stages in an amplifier cascade to increase the magnitude of the ECG signal as described in the '486 patent. The automatic gain control block 512 may also determine whether the ECG signal is experiencing distortion (e.g., soft clipping or hard clipping) and provide an indication of signal distortion. The electrode falloff sensing block 514 determines whether the electrodes have fallen off the patient and provides an electrode contact indicator. The electrode quality information provided by the HF noise analyzer block 510, the automatic gain control block 512, and the electrode falloff sensing block 514 may be received by the signal quality monitor 518. The signal quality monitor 518 analyzes the various parameters received by the HF noise analyzer 510, the automatic gain control 512, and the electrode falloff sensing block 514 to provide a final signal quality indicator to the decision logic block 520. It is appreciated that the signal quality monitor block 518 may also receive electrode quality information from the spectrum analyzer block 508 in the form of a low frequency (LF) noise indicator.

The QRS detector block 504, axis analyzer 506, and spectrum analyzer 508 each analyze the incoming electrode information 502 and generate heart rate information. The QRS detector block 504 determines the heart rate of the patient based on the electrode information 502. The QRS detector block 504 may also determine the heart rate stability of the patient based on heart rate changes. The QRS detector block 504 provides the determined heart rate and heart rate stability to the rate analyzer block 516. The axis analyzer block 506 may also determine the electrical axis of the heart of the patient using various morphology techniques. The axis analyzer block 506 provides an axis rate to the rate analyzer block 516. In addition, the axis analyzer block 506 determines the vector of the electrical axis of the heart and can output an axis validity signal indicating whether the patient is experiencing a treatable condition or a non-treatable condition. The various processes performed by the axis analyzer 506 are described in more detail below with reference to FIG. 6. The axis information is passed to the decision logic block 520 to determine whether the patient is experiencing an arrhythmia and/or identify the particular type of arrhythmia the patient is experiencing. The spectrum analyzer 508 measures and evaluates the frequency components of the electrode information 502. The spectrum analyzer 508 may transform the electrode information into the frequency domain by, for example, a Fast Fourier Transform (FFT). The spectrum analyzer 508 determines a spectral heart rate that is provided to the rate analyzer block 516.

The rate analyzer block 516 receives heart rate information from the QRS detector block 504, the axis analyzer block 506, and the spectrum analyzer block 508. The rate analyzer block 516 determines whether the patient is experiencing an elevated heart rate based on the heart rate information and provides an indication of the high heart rate to the decision logic block 520. The rate analyzer block 516 may determine the heart rate of the patient by determining whether the heart rates from the QRS detector 504 are equal across the electrode pairs (e.g., side-side electrode pair and front-back electrode pair). If the rates are equal, the rate analyzer block 516 may assume that heart rate from the QRS detector block 504 is the proper rate. However, if the rate stability signal begins to change or if the rates across the electrode pairs begin to differ, the rate analyzer block 516 can use the axis rate from the axis analyzer 506 or spectral rate from the spectrum analyzer to determine the proper heart rate. The rate analyzer block 516 can track the stability of the axis rate and the spectral rate to determine the reliability of the respective rates. In addition, the rate analyzer 516 can reevaluate the rate inputs individually and independently or in comparison to one another.

The decision logic 520 receives the indication of a high heart rate from the rate analyzer 516, an indication of axis validity from the axis analyzer 506, and a signal quality indicator from the signal quality monitor 518. The decision logic 520 employs the heart rate, heart axis, and signal quality information to determine whether the patient is experiencing an arrhythmia and/or identify the arrhythmia being experienced by the patient. For example, the decision logic block 520 may employ the signal quality indicator to determine the reliability of the heart axis information and heart rate information received from the axis analyzer 506 and rate analyzer 516, respectively. For example, the decision logic 520 may ignore information from the axis analyzer 506 and the rate analyzer 516 while the ECG signal quality is very poor.

In cases where the electrode information is of sufficient quality, the decision logic block 520 may determine whether the patient is experiencing an arrhythmia based on the heart axis information and heart rate information. For example, the decision logic 520 may employ the heart rate information to determine whether the patient is experiencing an arrhythmia and employ the heart axis information to discriminate between one or more types of arrhythmias. As described in more detail below with reference to the axis analyzer 506, a patient having peaks in correlation between the ECG template and the ECG signal of the patient at a different time than phase zero crossings in the correlation signal is likely experiencing an arrhythmia originating from a heart ventricle. Accordingly, the decision logic block 520 may analyze the axis information to discriminate between arrhythmias originating in a heart ventricle (e.g., ventricular tachycardia and ventricular fibrillation) and arrhythmias originating from other areas of the heart (e.g., supraventricular tachycardia).

Figure 6:
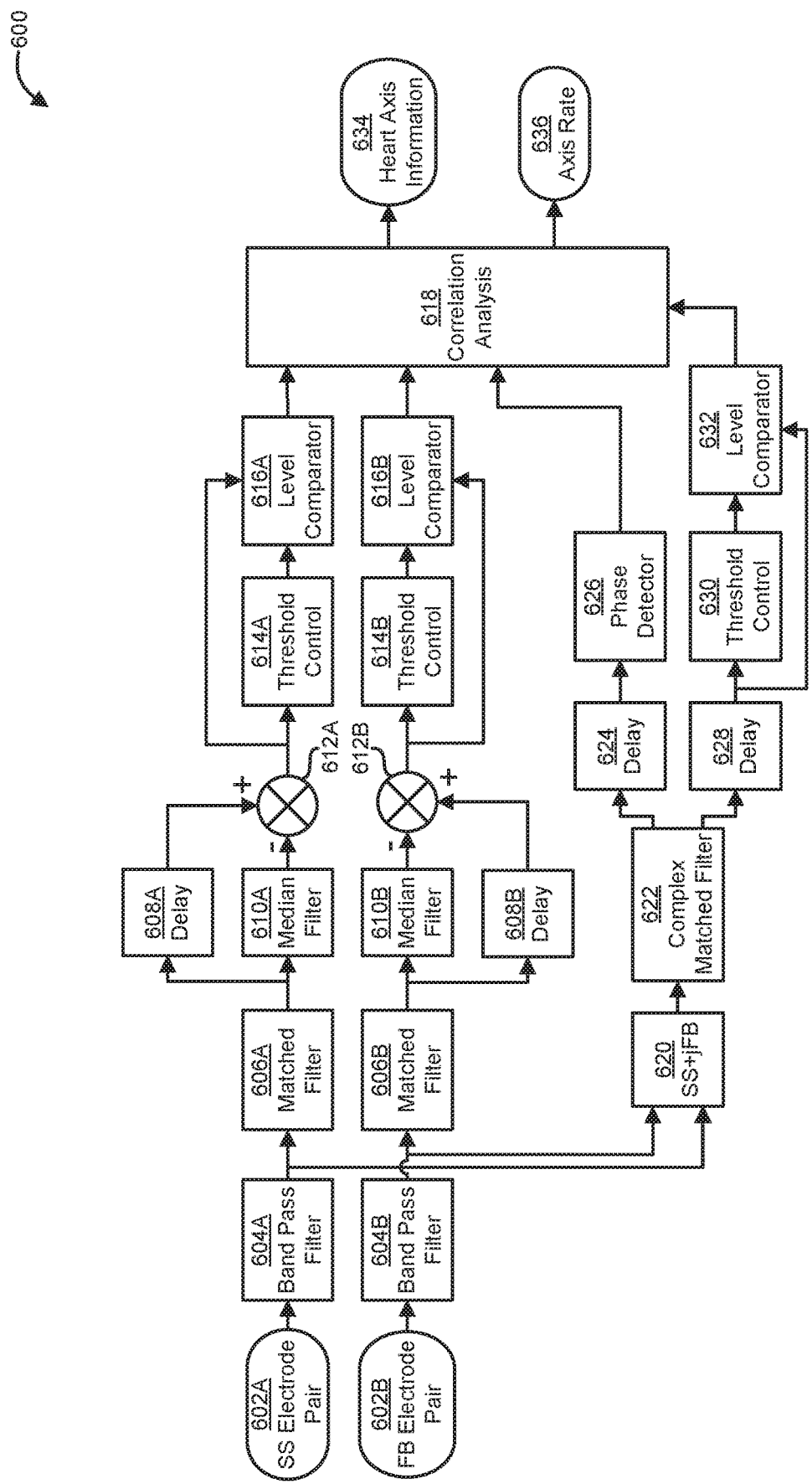
FIG. 6 is a block diagram of one example of an axis analyzer.

Referring to FIG. 6, a block diagram of an example axis analyzer 600 (e.g., axis analyzer 506) is illustrated. The axis analyzer 600 receives ECG input signals from one or more electrode pairs and employs morphology analysis techniques to analyze the electrical axis of the heart of the patient. The axis analyzer provides heart axis information 634 and axis rate information 636 to other components of, for example, the cardiac event detector 500. As discussed above with reference to the cardiac event detector 500, the blocks illustrated in the axis analyzer 600 may be implemented in hardware, software, or a combination of hardware and software.

As illustrated in FIG. 6, the axis analyzer 600 receives ECG signals from a side-side electrode pair 602A and a front-back electrode pair 602B. The ECG signals received from the side-side electrode pair 602A and the front-back electrode pair 602B are filtered by bandpass filters 604A and 604B, respectively, to remove any noise contained outside the frequency band of interest. The filtered ECG signals are passed to matched filters 606A and 606B to determine a correlation between the ECG signals of the patient and an ECG template of the patient. In addition, the filtered ECG signals are converted into a complex signal by the complex signal generator 620 and provided to the complex matched filter 622. As described above, the matched filters may be constructed based on various coefficients determined by the baseline generator 422 while the device is operating in a baselining mode.

Referring to the complex matched filter 622, the output includes a phase signal provided to delay block 624 and a magnitude signal provided to delay block 628. The delay blocks 624 and 628 delay the signal by a predetermined amount of time (e.g., seven sample periods). The delay blocks 624 and 628 allow the output of the level comparator blocks 616A, 616B, and 632 and phase detector block 626 to be in time sync. Accordingly, the particular delay employed may vary based on the particular architecture of the axis analyzer 600. The phase detector 626 continuously monitors the phase signal received from the delay block 624 and identifies zero crossings in the phase signal. The phase detector 626 provides a signal to the correlation test block 618 responsive to detecting a zero crossing in the phase signal. The threshold control block 630 receives the magnitude signal delay block 628 and determines a threshold to be employed by the level comparator 632 based on the history of the magnitude signal. The level comparator 632 compares the magnitude signal from the delay block 628 with the threshold set by threshold control block 630. The level comparator 632 provide a signal to the correlation test block 618 that indicates a peak detection in the magnitude signal responsive to the magnitude signal being above the threshold. Returning to the threshold control block 630, the threshold may be permitted to vary within a preset range of values. In some cases, the threshold may be set to less than 90% of previously detected peak levels. Adjustment of the threshold allows the axis analyzer 600 to track variations in the correlation caused by, for example, changes in received signal quality. Adjusting the threshold also may be employed to control the sensitivity of the axis detector.

Returning to matched filters 606A and 606B, the output correlations of the matched filters 606A and 606B are provided to median filters 610A and 610B, respectively. The median filters 610A and 610B determine the median of the magnitude values provided by the matched filters 606A and 606B. The median values determined by the median filters 610A and 610B are subtracted from the correlations from the matched filters, after being delayed by delay blocks 608A and 608B to keep in time sync, in summation blocks 612A and 612B, respectively. Removing the median values from the correlation may help to distinguish correlation peaks. The summation blocks 612A and 612B may also apply a floor operator of zero to convert any negative values to zero. It is appreciated that the summation blocks 612A and 612B may be implemented in a DSP by, for example, subtracting two values and applying a floor operator or by circuit components by, for example, a summation circuit followed by a rectification circuit.

The output from the summation blocks 612A and 612B is provided to threshold control blocks 614A and 614B that each generate a threshold for level comparator blocks 616A and 616B, respectively. As described above with reference to threshold control block 630 and level comparator 632, the threshold control blocks 614A and 614B adjust the threshold for determining a peak in magnitude based on previous correlation peak values. The level comparator blocks 616A and 616B provide signals to the correlation test block 618 indicative of whether a peak in correlation was detected.

The correlation analysis block 618 examines the timing relationship of the output of phase detector 626 (e.g., the timing of phase zero crossings) and level comparators 616A, 616B, and 632 (e.g., the timing of magnitude peaks) and provides heart axis information 634 to other blocks within, for example, cardiac event detector 500. Patients with a normal sinus rhythm generally have a peak in correlation magnitude at approximately the same time as a phase zero crossing. As the timing of the peaks in magnitude separates from the timing of zero crossings, the likelihood of the patient experiencing a cardiac event increases. The correlation analysis block 618 examines the timing and determines whether a treatable condition exists based on the timing information. For example, the correlation analysis block 618 may identify erratic changes in timing associated with cardiac events. The occurrence of a single magnitude peak at a given instant of time, that does not have a corresponding zero phase crossing point, may not be significant. However, a phase shift away from the magnitude peaks that is maintained over a period of time or an erratically shifting phase variation may be significant. Example patient sinus rhythms and the associated correlations are illustrated in U.S. Pat. No. 5,944,669, titled "APPARATUS AND METHOD FOR SENSING CARDIAC FUNCTION" and issued on Aug. 31, 1999, which is hereby incorporated herein by reference in its entirety. The correlation analysis block 618 may analyze the characteristics of the timing shift to determine whether the arrhythmia is a treatable arrhythmia (e.g., ventricular tachycardia or ventricular fibrillation) or a non-treatable arrhythmia (e.g., supraventricular tachycardia). For example, the ventricular response is not greatly affected in a supraventricular tachycardia originating in the atrium (although the heart rate may increase). Therefore, a radical shift between the phase zero crossings and the magnitude peaks does not occur. The ventricular response, however, in ventricular tachycardia or ventricular fibrillation is directly impacted and a radical shift between the phase zero crossings and the magnitude peaks generally occurs.

Example Cardiac Detection

Having described various system architectures that may be suitable for the cardiac event detector 424 to detect cardiac events based on an ECG template, various example processes implemented by the cardiac detector 424 will now be described. In some of these example processes, a cardiac event detector, such as the cardiac event detector 424, selects an appropriate ECG template to utilize in morphology analysis. For example, the device may include multiple ECG templates corresponding to different persons in a household. In some implementations, prior to use, the patient, family member, or other caregiver may be prompted to select the appropriate person for whom the device is to be configured such that the appropriate ECG template is selected. In some examples, the cardiac event detector 424 can detect a patient ECG signal and based on the detected ECG signal automatically determine the appropriate ECG template (e.g., the ECG template corresponding to the person being monitored) to use for the monitoring. For example, the cardiac event detector 424 may base a determination of the appropriate ECG template on the detection of one or more features in the ECG signal. For example, a first member of a household may have certain recurring ECG features or morphology that are/is different from ECG features or morphology in a second member of a household. Such features can include, without limitation, a width and height of the QRS complex, the prominence of the T wave, and a length and/or ST segment.

In addition, at least one of these example processes includes possible actions the cardiac event detector 424 may initiate upon detection of a cardiac event. Referring to FIG. 8, an example patient monitoring process 800 is illustrated as performed by, for example, a cardiac event detector, such as the cardiac event detector 424. The patient monitoring process 800 includes the acts of receiving patient ECG information 802, selecting an ECG template 804, and comparing the patient ECG information with the selected ECG template 806. In some examples, the medical device is a medical device capable of providing therapy to the patient and the patient monitoring process 800 includes the act of providing therapy to the patient 808.

In act 802, the cardiac event detector receives ECG information from, for example, one or more ECG electrodes attached to the patient. The ECG information may include, for example, a digitized ECG signal.

In act 804, the cardiac event detector selects an ECG template to compare with the ECG information of the patient. In some examples, the cardiac event detector may select a template associated with the particular patient connected to the medical device. The cardiac detector may uniquely identify the patient based on a configurable parameter or one or more characteristics of the received ECG information. It is appreciated that the cardiac event detector may select a particular ECG template based on parameters other than patient identity. For example, the cardiac detector may filter the patient ECG signal through the various matched filters associated with the ECG templates stored in memory and select the ECG template associated with the matched filters that yielded the highest correlation values. For example, the detector may build a composite ECG signal based on averaging detected ECG data points over a period a time (e.g., 20 seconds). The detector can then compare each averaged point with a corresponding point in the ECG template and calculate a corresponding error value. The detector can select an ECG template associated with the lowest error value (e.g., based on a lowest mean error rate). It should be understood that any technique for calculating an average deviation from the ECG template coefficients may be used.

In some cases, the patient may have been recently administered a shock, and as a result his or her ECG signal may differ characteristically from the ECG signal prior to the shock event. As a result, the patient may need to be re-baselined in accordance with the principles described herein. Accordingly, the template selection process 900 may use the newly obtained ECG template for comparison purposes. Additional example template selection processes are described below with reference to FIGS. 9 and 10.

In act 806, the cardiac event detector compares the received ECG information with the selected ECG template to determine whether the patient is experiencing a cardiac condition. The cardiac event detector may perform the comparison by employing one or more matched filters as described above with reference to FIGS. 5 and 6. The cardiac event detector may identify a particular type of arrhythmia based on the comparison and/or determine whether the arrhythmia is a treatable arrhythmia. For example, an arrhythmia originating from a heart ventricle (e.g., ventricular tachycardia and ventricular fibrillation) may be a treatable arrhythmia while an arrhythmia originating from above the ventricular (e.g., supraventricular tachycardia) may be an untreatable arrhythmia.

In some examples, the cardiac event detector (in act 806) may compare the selected ECG template to the patient ECG signal of the patient by determining deviations in the PQRST points of the patient ECG signal and the template. The cardiac event detector may identify one or more cardiac events based on the deviations. For example, the cardiac event detector may determine that the T wave of the patient's ECG signal is inverted relative to the ECG template and the QRS wave of the patient's ECG is wider relative to the ECG template. In this example, the cardiac event detector may identify these deviations as an occurrence of premature ventricular contraction (PVC). It is appreciated that other cardiac events may be detected based on the deviations of the patient ECG signal.

In some examples where the medical device is capable of providing therapy to the patient, the cardiac event detector may perform act 808 and provide therapy to the patient. In act 808, the cardiac event detector may only provide treatment to the patient if a treatable cardiac event is detected and may withhold treatment to the patient if an untreatable arrhythmia is detected. Various alarms may be provided to the patient during the therapy administration process as described in U.S. Patent Publication No. 2015/0039053, titled "SYSTEMS AND METHODS OF DELIVERY THERAPY USING AN AMBULATORY MEDICAL DEVICE" filed on Jun. 27, 2014, which is hereby incorporated herein by reference in its entirety.

FIG. 9 illustrates an example ECG template selection process 900 performed by, for example, a cardiac event detector such as the cardiac event detector 424. In one example, the cardiac event detector, when executing the ECG template selection process 900, selects an appropriate template based on the state of the patient. For example, the cardiac event detector executing the template selection process 900 may determine that the patient is active (e.g., exercising) and select an ECG template associated with active state of the patient.

As illustrated in FIG. 9, the template selection process 900 includes acts of receiving patient information 902, determining a current patient state 904, and selecting an ECG template associated with the patient state 906.

In act 902, the cardiac event detector receives patient information. The patient information may include, for example, motion information from an accelerometer included in or operatively connected to the medical device. For example, such motion information can be used in the next act (act 904) to determine an activity level of the patient.

In act 904, the cardiac event detector determines the current state of the patient. For example, the cardiac event detector may determine that the patient is in an active state (e.g., exercising) or a resting state (e.g., sitting) based on the motion information. The cardiac event detector may determine the state based on the motion information by monitoring the amount of exercise the patient performed within a predetermined period of time and assigning an activity score to the patient based on the amount of exercise.

In act 906, the cardiac event detector selects an ECG template associated with the current state of the patient. For example, the cardiac event detector may determine that the patient is in an active state in act 904 (e.g., by noting that the activity score has exceeded a threshold activity score) and select the ECG template associated with the active state. For example, the threshold activity score can be a parameter than can be predetermined and set by a caregiver or a technician. The cardiac event detector may also compare the activity score generated in act 904 with one or more activity scores associated with each ECG template and select the ECG template with the closest activity score.

In other examples, a detector can average in real-time ECG data points (e.g., corresponding to the PQ, QRS, and ST segments) over a predetermined period of time to build an ECG composite. The detector can then compare each averaged point in the ECG composite with a corresponding point in the current ECG template and calculate a corresponding error value. The detector may perform a similar comparison with other ECG templates stored in device memory. The detector can then select an ECG template associated with the lowest error value (e.g., based on a lowest mean error rate). It should be understood that any technique for calculating an average deviation from the ECG template coefficients may be used to determine an appropriate ECG template to use for real-time monitoring.

In some situations, before using a selected ECG template, the device can alert and/or upload to a central server the selected ECG template for review and approval by the patient's caregiver. For example, when the device determines that a new template is needed for the patient based, for example, on detecting a deviation above a certain threshold (e.g., more than 5-10% difference in magnitude comparison and/or phase comparison), the device can alert the patient's caregiver. The caregiver can then either be prompted to review and approve a new ECG template, or be provided an ability to re-baseline the patient. For example, the device can provide the caregiver an ability to re-baseline the patient remotely without requiring the patient to return to the caregiver's office.

FIG. 10 illustrates another example template selection process 1000 performed by, for example, a cardiac event detector such as the cardiac event detector 424. In one example, the cardiac event detector, when executing the template selection process 1000, compares multiple ECG templates to select an appropriate template. For example, if there is a substantial deviation between the initial and subsequent ECG templates, then each template can be evaluated against the incoming ECG signal for determining which of the templates may be a better fit to the patient ECG information. As noted above, the various ECG templates may be ECG templates generated for the same patient at different times to track changes in the normal sinus rhythm of the patient.

The template selection process 1000 can include the acts of comparing the initial ECG template with a subsequent ECG template 1002, determining whether there is a substantial deviation between the templates 1004, selecting an initial ECG template 1006, and selecting an ECG template with a better fit to the patient ECG information 1008.

In act 1002, the cardiac event detector compares the initial ECG template with a subsequent (e.g., a new or a proposed) ECG template. The ECG templates may be templates formed by the baseline generator 422 based on ECG signals from the patient at different times (e.g., 2 weeks apart). As is appreciated by a person of ordinary skill in the art, given the benefit of this disclosure, various methods may be employed to compare ECG templates. For example, the matched filter coefficients, frequency response, and/or impulse response associated with the matched filters of the ECG templates may be compared. In another example, the cardiac event detector may filter the ECG signal of the patient with the matched filters from the respective ECG templates and compare the ECG templates by comparing the filtered ECG signal. In act 1004, the cardiac event detector determines whether there is a substantial deviation between the two ECG templates. Various methods may be employed to determine the similarity between the two templates. For example, the difference between the matched filter coefficients, frequency response, and/or impulse response of the matched filters associated with the respective ECG templates may be compared with one or more thresholds. In one example, the matched filter coefficients of each template may be averaged and a difference between the averages from each template may be compared with a threshold. In another example, the cardiac event detector filters the ECG signal of the patient with the matched filters of the respective ECG templates and assigns a quality score to each template based on the correlation values output by the matched filters. In this example, the difference between the quality scores associated with the respective ECG templates may be compared with a threshold. The threshold difference between the ECG templates may be generated by the cardiac detector based on, for example, a maximum rate of change of normal human sinus rhythms.

For example, the detector may compare two ECG templates by calculating a series of error values corresponding to the individual template coefficients. Then, the detector can determine if a measure of the error values exceeds a predetermined threshold, e.g., by calculating an root mean square (RMS) average of the determined error scores and determining if there is more than, e.g., a 10-20% deviation between a current ECG template and a proposed ECG template to replace the current ECG template. It should be understood that any other technique for calculating an average deviation of the patient ECG information from the ECG template coefficients may be used.

If the cardiac event detector determines that the two templates are substantially different, the cardiac event detector proceeds to act 1006 and selects the initial ECG template. Selecting the initial template in act 1006 may also include deleting the subsequent ECG template and/or replacing the initial template with the subsequent ECG template. Otherwise the cardiac event detector proceeds to act 1008 and selects the ECG template with the best fit to the ECG signal of the patient.

In act 1008, the cardiac event detector selects the ECG template with the best fit to the ECG signal of the patient. Various methods may be employed to compare the ECG signal of the patient with the ECG templates. For example, the cardiac event detector may filter the ECG signal of the patient with one or more matched filters from each ECG template and determine a quality score representative of the match quality between the matched filter and the ECG signal. The quality score may be generated based on the correlations values output by the matched filters filtering the ECG signal of the patient. The cardiac event detector may select the ECG template associated with the matched filter that yielded the highest quality score. By way of example, a measure of a deviation from zero phase crossing and/or magnitude threshold for current patient ECG information can be used as a quality score for a particular ECG template.

Example Mode Selector

Returning to FIG. 4, the mode selector 420 controls the operating mode of the medical device. For example, the mode selector 420 may determine whether the medical device operates in a baselining mode or a monitoring mode. The mode selector 420 may select the current operating mode on a variety of parameters. For example, the mode selector 420 may select the current operating mode based on a configurable parameter received from an external entity (e.g., the patient). In addition, the mode selector 420 may automatically enter baselining mode on a periodic or aperiodic schedule. Accordingly, the particular criteria employed by the mode selector 420 to determine the operating mode may vary based on the particular implementation of the medical device.

Figure 11:
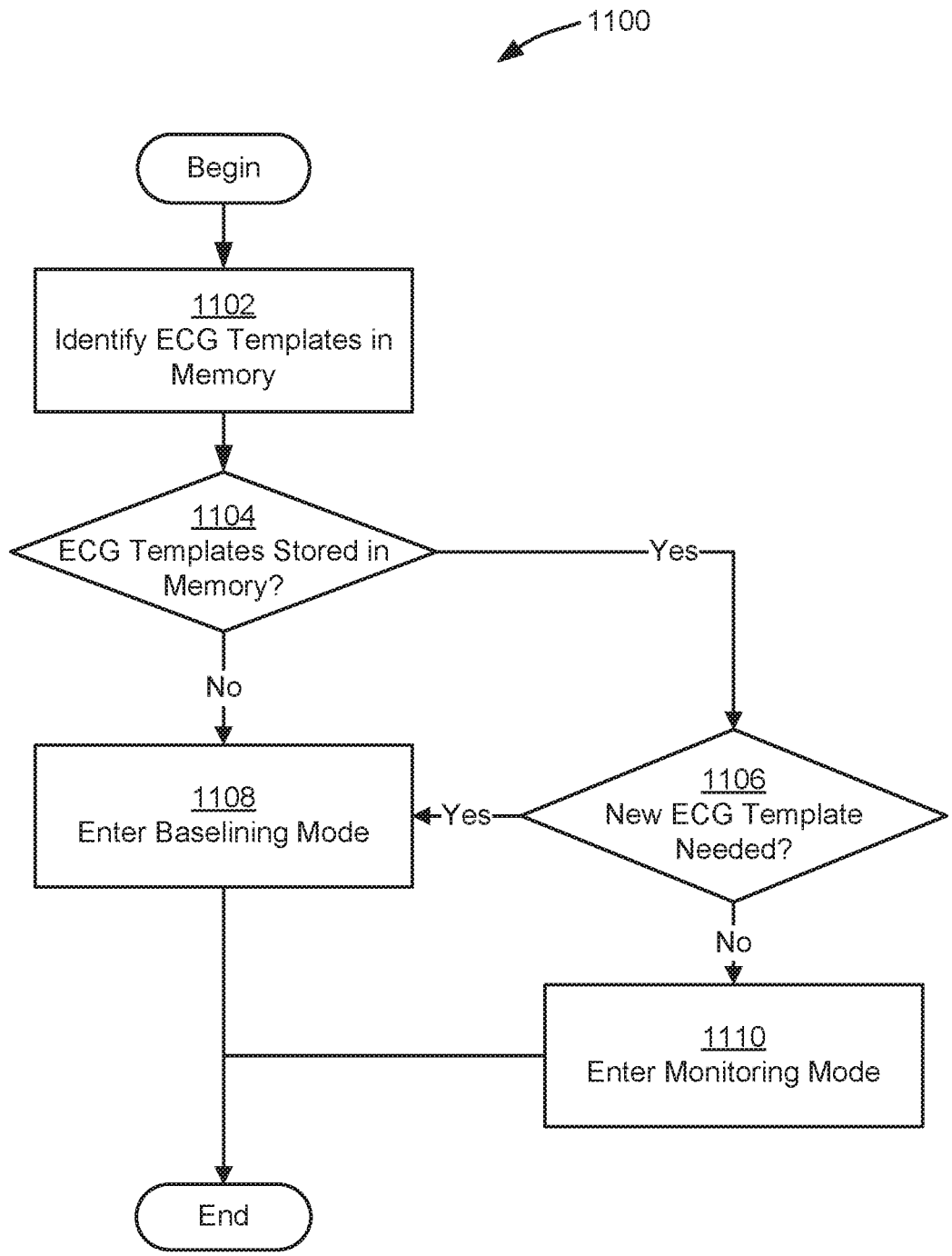
FIG. 11 is a flow diagram of an example mode selection process.

FIG. 11 illustrates an example mode selection process 1100 performed by, for example, a mode selector such as the mode selector 420. The mode selector 420 may execute the mode selection process 1100 upon a medical device being turned on to identify an appropriate mode for the medical device to initially employ. The mode selection process 1100 includes acts of identifying ECG templates stored in memory 1102, determining whether any ECG templates are stored in memory 1104, determining whether new ECG templates are needed 1106, entering baselining mode 1108, and entering monitoring mode 1110.

In act 1102, the mode selector identifies any ECG templates stored in memory. The ECG templates may be stored in, for example, the patient data 416.

In act 1104, the mode selector determines whether any ECG templates are stored in memory. If no ECG templates are stored in memory, the mode selector proceeds to act 1108 and enters baselining mode. Otherwise, the mode selector proceeds to act 1106 and determines whether new ECG templates are needed.

In act 1106, the mode selector determines whether new ECG templates are needed based on one or more criteria. For example, the mode selector may identify a creation date for any ECG templates stored in the memory determine that a new ECG template is needed because the stored ECG templates are older than a predetermined value (e.g., older than 2 weeks). If the mode selector determines that a new ECG template is needed, the mode selector proceeds to act 1108 and enters baselining mode. Otherwise, the mode selector proceeds to act 1110 and enters monitoring mode.

In some examples, the mode selector may determine that a new ECG template is needed in act 1106 based on a number of false positive arrhythmia detections and/or a number of confirmed arrhythmia detections. The detected arrhythmias may be confirmed by analyzing the patient movement, as sensed by a motion detector for example, during periods in which an arrhythmia is detected. During an arrhythmia, the patient likely has irregular bodily movements due to, for example, the patient falling and/or becoming unconscious. Accordingly, in some examples, a false positive arrhythmia may be identified by detecting regular patient movement (e.g., the patient is walking normally) during a period in which an arrhythmia is detected. A confirmed arrhythmia may be identified by detecting irregular patient movement (e.g., the patient fell) during a period in which an arrhythmia is detected. In addition, arrhythmias may also be confirmed based on user interaction with the medical device after an arrhythmia is detected. For example, the medical device, in some examples, may include one or more buttons operable by the patient to delay the administration of therapy and/or silence an alarm (e.g., response buttons 210 illustrated above in FIG. 2). In this example, the medical device may determine that the detected arrhythmia was a false positive when user interaction with the one or more buttons is detected. The mode selector may compare the number of confirmed arrhythmia detections and/or the number of false positive arrhythmia detections with a threshold specified by a configurable parameter to determine whether a new template is needed. For example, the mode selector may automatically identify that a new template is needed after two false positive arrhythmia detections. In another example, the mode selector may subtract the number of false positive arrhythmia detections from the number of confirmed arrhythmia detections and compare the difference with a threshold.

Having thus described several aspects of at least one example of this disclosure, it is to be appreciated various alterations, modifications, and improvements will readily occur to those skilled in the art. Such alterations, modifications, and improvements are intended to be part of this disclosure, and are intended to be within the scope of the disclosure. Accordingly, the foregoing description and drawings are by way of example only.

What is claimed is:

1. A medical device comprising:
   at least one electrode to sense an electrocardiogram (ECG) signal of a patient; and
   a controller coupled to the at least one electrode, the controller being configured to:
   generate a first ECG template based on a first ECG signal of the patient received during a first baselining operation, wherein generating the first ECG template comprises storing the first ECG signal and determining a plurality of first filter parameters using the first ECG signal,
   determine that the patient has been administered a therapeutic shock,
   responsive to the determination that the patient has been administered the therapeutic shock, initiate a second baselining operation,
   generate a second ECG template based on a second ECG signal of the patient recorded after the administration of the therapeutic shock and received during the second baselining operation, wherein generating the second ECG template comprises storing the second ECG signal and determining a plurality of second filter parameters using the second ECG signal, and
   determine whether the patient is experiencing a cardiac event based on a comparison of the second ECG template to a real time ECG signal received during real time monitoring of the patient.

2. The medical device of claim 1, wherein the first baselining operation is performed before active patient monitoring begins.

3. The medical device of claim 1, wherein the at least one electrode further comprises multiple pairs of ECG electrodes comprising a front-back electrode pair and a side-side electrode pair.

4. The medical device of claim 3, wherein at least one of the first or second ECG templates is a composite template comprising a combined average ECG signal from the front-back electrode pair and the side-side electrode pair.

5. The medical device of claim 1, wherein at least one of the first or second ECG signals comprises two minutes of ECG data.

6. The medical device of claim 1, wherein the controller is configured to transmit information to a remote system regarding the first ECG template and the second ECG template.

7. The medical device of claim 6, wherein the controller is configured to receive approval from the remote system to use one or more of the first ECG template or the second ECG template.

8. The medical device of claim 6, wherein the controller is configured to generate the second ECG template during a baselining operation initiated by one of a remote server, a user input, or a patient input.

9. The medical device of claim 1, wherein the determination of whether the patient is experiencing a cardiac event by the controller comprises execution of a convolution operation on the real time ECG signal and the second ECG template to determine whether one or more characteristics of the real time ECG signal indicate either a presence or absence of the cardiac event.

10. The medical device of claim 1, wherein the controller is configured to provide a notification prior to generating at least one of the first ECG template or the second ECG template.

11. The medical device of claim 1, wherein the controller is configured to determine whether the patient is experiencing the cardiac event in part based on one or more morphological differences between the real time ECG signal and the second ECG template.

12. The medical device of claim 1, wherein the controller is configured to
   determine numerical coefficients of one or more matched filters of the second ECG signal of the second ECG template, and
   determine whether the patient is experiencing the cardiac event based in part by filtering the real time ECG signal with the one or more matched filters.

13. The medical device of claim 1, wherein the controller is configured to determine whether the cardiac event is a treatable arrhythmia or an untreatable arrhythmia by performing a morphology analysis of the real time ECG signal with respect to the second ECG template.

14. The medical device of claim 13, wherein the morphology analysis comprises detecting a QRS complex in the real time ECG signal, and responsive to detecting the QRS complex, determining that the cardiac event is an untreatable arrhythmia.

15. The medical device of claim 14, wherein detecting the QRS complex comprises performing a convolution operation on the real time ECG signal and the second ECG signal of the second ECG template to determine whether one or more characteristics in the real time ECG signal indicates either a presence or an absence of the QRS complex.

16. The medical device of claim 13, wherein the treatable arrhythmia includes either ventricular tachycardia or ventricular fibrillation and wherein the untreatable arrhythmia includes supraventricular tachycardia.

17. A medical device comprising:
   at least one electrode to sense an electrocardiogram (ECG) signal of a patient; and
   a controller coupled to the at least one electrode, the controller being configured to
      generate a first ECG template based on a first ECG signal of the patient received during a baselining operation,
      generate a second ECG template based on a second ECG signal of the patient,
      transmit the first ECG template to an external system,
      receive, from the external system, an indication by a caregiver of the patient concerning the first ECG template, wherein the indication comprises an approval of the first ECG template,
      identify, based on the indication, one of the first ECG template and the second ECG template, and
      determine whether the patient is experiencing a cardiac event based on a real time ECG signal of the patient and the identified one of the first ECG template and the second ECG template.

18. The medical device of claim 17, wherein the controller is further configured to
   determine that the patient has been administered a therapeutic shock,
   responsive to the determination that the patient has been administered the therapeutic shock, initiate a second baselining operation, and
   generate the second ECG template based on the second ECG signal of the patient received during the second baselining operation.

19. The medical device of claim 18, wherein at least one of the first or second ECG signals comprises two minutes of ECG data.

20. The medical device of claim 17, wherein the baselining operation is performed before active patient monitoring begins.

* * * * *